US009453203B2

(12) United States Patent
May et al.

(10) Patent No.: US 9,453,203 B2
(45) Date of Patent: Sep. 27, 2016

(54) METHODS AND VECTORS FOR CELL IMMORTALISATION

(75) Inventors: Tobias May, Braunschweig (DE);
Hansjörg Hauser, Wolfenbüttel (DE);
Franziska Klein, Braunschweig (DE);
Jeannette Zauers, Vechelde (DE);
Roland Schucht, Braunschweig (DE)

(73) Assignee: Helmholtz-Zentrum Fur Infektionsforschung, Braunschweig (DE)

( * ) Notice: Subject to any disclaimer, the term of this patent is extended or adjusted under 35 U.S.C. 154(b) by 0 days.

(21) Appl. No.: 13/882,709

(22) PCT Filed: Nov. 2, 2011

(86) PCT No.: PCT/EP2011/005528
§ 371 (c)(1),
(2), (4) Date: Jun. 7, 2013

(87) PCT Pub. No.: WO2012/059223
PCT Pub. Date: May 10, 2012

(65) Prior Publication Data
US 2013/0273550 A1 Oct. 17, 2013

Related U.S. Application Data

(60) Provisional application No. 61/409,503, filed on Nov. 2, 2010.

(30) Foreign Application Priority Data

Nov. 2, 2010 (EP) ..................................... 10014200

(51) Int. Cl.
*C12N 5/071* (2010.01)
*C07K 14/47* (2006.01)
*C07K 14/82* (2006.01)
*C12N 5/00* (2006.01)
*A61K 38/00* (2006.01)

(52) U.S. Cl.
CPC ............... *C12N 5/067* (2013.01); *C07K 14/47* (2013.01); *C07K 14/4738* (2013.01); *C07K 14/82* (2013.01); *C12N 5/00* (2013.01); *C12N 5/0602* (2013.01); *A61K 38/00* (2013.01); *C12N 2501/155* (2013.01); *C12N 2510/04* (2013.01); *C12N 2740/15043* (2013.01)

(58) Field of Classification Search
CPC .. C07K 14/47; C07K 14/4738; C07K 14/82; C12N 5/00; C12N 5/0602; C12N 5/067; C12N 2510/04; C12N 2740/15043; C12N 2501/155; A61K 38/00
See application file for complete search history.

(56) References Cited

U.S. PATENT DOCUMENTS

2010/0190250 A1* 7/2010 Hu ................................. 435/377
2013/0273550 A1* 10/2013 May et al. .................... 435/6.12

FOREIGN PATENT DOCUMENTS

| WO | WO 9624669 | 8/1996 |
| WO | WO 0056158 | 9/2000 |
| WO | WO 0166781 | 9/2001 |
| WO | WO 03001198 | 1/2003 |
| WO | WO 03035879 | 5/2003 |
| WO | WO 2005012513 | 2/2005 |
| WO | WO 2005042728 | 5/2005 |
| WO | WO 2006048228 | 5/2006 |
| WO | WO 2010000491 | 1/2010 |
| WO | WO 2010007593 | 1/2010 |

OTHER PUBLICATIONS

Takahashi, et al. (2007) "Induction of Pluripotent Stem Cells from Adult Human Fibroblasts by Defined Factors", Cell, 131: 861-72.*
Li, et al. (1996) "Host range restrictions of oncogenes: myc genes transform avian but not mammalian cells and mht/raf genes transform mammalian but not avian cells", Proceedings of the National Academy of Science, USA, 93(15): 7522-27.*
Wang, et al. (1993) "Bone morphogenetic protein-2 causes commitment and differentiation in C3H10T1/2 and 3T3 cells", Growth Factors, 9(1): 57-71, Abstract Only.*
Loh et al., Cell Cycle. Apr. 1, 2008; 7(7):885-91. Molecular framework underlying pluripotency.*
Maherali and Hochedlinger, Cell Stem Cell. Dec. 4, 2008; 3(6):595-605. Guidelines and techniques for the generation of induced pluripotent stem cells.*
Preston, et al. (1996) "Induction of Apoptosis by c-Fos protein", Molecular and Cellular Biology, 16(1): 211-18.*
http://sciencenetlinks.com/student-teacher-sheets/cells-your-body/ (2014) "The Cells in Your Body", AAAS Science NetLinks, Published online by AAAS, NY, New York, no author, no volume, no journal number, 2 pages long.*
Cimadamore, et al. (2013) "SOX2—LIN28/let-7 pathway regulates Proliferation and neurogenesis in neural precursors", Proceedings of the National Academy of Science, USA., 110(32): E3017-26.*
Supplemental Data for Takahashi, et al. (2007) "Induction of Pluripotent Stem Cells from Adult Human Fibroblasts by Defined Factors", Cell, 131: 861-72, cited as: Cell, vol. 126, Supplemental Data Induction of Pluripotent Stem Cells from Mouse Embryonic and Adult Fibroblast Cultures by Defined Factors, by Takahashi et al., 41 pages (online only).*
Yu, et al. (2006) "Human Induced Pluripotent Stem Cells Free of Vector and Transgene Sequences", Science, 324: 797-801.*
http://en.wikipedia.org/wiki/Mammal, published by Wikipedia, San Francisco, CA, authors unknown, no journal, no volume, no issue, downloaded Feb. 26, 2015, 14 pages long.*
Takahashi and Yamanaka, "Induction of Pluripotent Stem Cells from Mouse Embryonic and Adult Fibroblast Cultures by Defined Factors", Cell, 126(4): 663-73.*

(Continued)

*Primary Examiner* — Robert M Kelly
(74) *Attorney, Agent, or Firm* — Barnes & Thornburg LLP; Yonghao Hou

(57) ABSTRACT

The present invention relates to a method and to vectors for the immortalisation of cells independent of their type. It further relates to a cell or a cell line produced with the method or the vectors of the invention. The invention also relates to the use of this cell or cell line in in vitro applications and in the treatment of disease.

2 Claims, 10 Drawing Sheets

(56) References Cited

OTHER PUBLICATIONS

Akimov S S et al: "Bypass of senescence, immortalization, and transformation of human hematopoietic progenitor cells", Stem Cells, Alphamed Press, Dayton, OH, vol. 23, No. 9, Jan. 1, 2005, pp. 1423-1433, XP003016584, ISSN: 1066-5099, DOI: 10.1634/Stemcells, 2005-0390.

Hong Sunghoi et al.: "Functional analysis of various promoters in lentiviral vectors at different stages of in vitro differentiation of mouse embryonic stem cells", Molecular Therapy, Academic Press, San Diego, CA, vol. 15, No. 9, Sep. 1, 2007, pp. 1630-1639, XP002525058, ISSN: 1526-0016, DOI: 10.1038/SJ.MT.6300251.

Zhang et al: "Papillomavirus type 16 E6/E7 and human telomerase reverse transcriptase in esophageal cell immortalization and early transformation", Cancer Letters, New York, NY, vol. 245, No. 1-2, Dec. 22, 2006, pp. 184-194, XP005813559, ISSN: 0304-3835, DOI: 10.1016/J.Canlet.2006.01.005.

Mathas S et al: "Intrinsic inhibition of transcription factor E2A by HLH proteins ABF-1 and ID2 mediates reprogramming of neoplastic B cells in Hodgkin lymphoma", Nature Immunology, Nature Publishing Group, GB, vol. 7, No. 2, Feb. 1, 2006, pp. 207-215, XP009079152, ISSN: 1529-2908, DOI: 10.1038/NI1285.

Salmon P et al: "Reversible Immortalization of human primary cells by lentivector-mediated transfer of specific genes", Molecular Therapy, Academic Press, San Diego, CA, vol. 2, No. 4, Oct. 1, 2000, pp. 404-414, XP001028604, ISSN: 1525-0016, DOI: 10.1006/MTHE.2000.0141.

Bernard O et al: "Role of the C-MYC and the N-MYC proto-oncogenes in the immortalization of neural precursors", Journal of Neuroscience Research, Wiley-Liss, vol. 24, No. 1, Jan. 1, 1989, pp. 9-20, XP001010016, ISN: 0360-4012, DOI: 10.1002/JNR. 490240104.

Junying Yu et al.: "Human Induced Pluripotent Stem Cells Free of Vector and Transgene Sequences", NIH Public Access Author Manuscript, Science, May 8, 2009; 324(5928); 797-801. Doi:10. 1126/science1172482.

Japanese Patent Office, Translation of the Decision(Rejection), pp. 1-4.

* cited by examiner

| # | genes | first round | | | second round | | | | third round | | | |
|---|---|---|---|---|---|---|---|---|---|---|---|---|
| 1 | Id2 | 1 | 0 | 1 |  |  |  | 1 | 1 | 1 | 1 | 1 |
| 2 | Fos | 1 | 1 | 1 |  |  | 1 | 1 | 1 | 1 |  |  |
| 3 | NS1 | 0 | 0 | 0 |  |  | 0 | 0 |  |  |  |  |
| 4 | Jun | 0 | 0 | 0 |  |  | 0 | 0 |  |  |  |  |
| 5 | E2F1 | 0 | 0 | 0 |  |  | 0 | 0 |  |  |  |  |
| 6 | βCat | 0 | 0 | 0 |  |  | 0 |  |  |  |  |  |
| 7 | TAg | 0 | 0 |  |  |  | 0 |  |  |  |  |  |
| 8 | Myc | 1 | 0 | 0 |  |  | 1 |  |  |  |  |  |
| 9 | Id3 | 1 | 1 | 1 |  |  |  |  |  |  |  |  |
| 10 | E7 | 1 | 0 | 0 |  | 1 | 0 |  |  |  |  |  |
| 11 | E6 | 0 | 0 | 0 | 1 |  | 1 |  |  |  |  |  |
| 12 | Bcl2 | 0 |  | 0 |  |  |  |  |  |  |  |  |
| 13 | HoxA9 | 0 | 1 |  |  |  |  |  |  |  |  |  |
| 14 | Bmi1 | 0 | 0 | 0 |  |  |  |  |  |  |  |  |
| 15 | PymT | 0 | 0 | 0 |  | 1 |  |  |  |  |  |  |
| 16 | Core | 0 | 0 | 0 | 1 |  |  |  |  |  |  |  |
| 17 | Oct3 | 0 | 0 | 0 |  |  |  |  |  |  |  |  |
| 18 | Klf4 | 1 | 1 | 0 |  |  |  |  |  |  |  |  |
| 19 | Id1 | 1 | 1 | 0 | 1 | 1 | 1 | 1 | 1 | 1 | 1 | 1 |
| 20 | Myc | 0 | 0 | 0 | 1 | 1 | 1 | 1 | 1 | 1 | 1 | 1 |
| 21 | Lmo2 | 0 | 1 |  |  |  |  |  |  |  |  |  |
| 22 | Nk2l.2 | 1 | 1 | 0 |  |  |  |  |  |  |  |  |
| 23 | Yap1 | 0 | 0 | 0 |  |  |  |  |  |  |  |  |
| 24 | Nanog | 1 | 1 | 0 |  |  |  |  |  |  |  |  |
| 25 | Sox2 | 0 | 0 | 0 |  |  |  |  |  |  |  |  |
| 26 | RhoA | 0 | 1 | 0 |  |  |  |  |  |  |  |  |
| 27 | Ezh2 | 0 | 0 | 0 |  |  |  |  |  |  |  |  |
| 28 | Gli1 | 0 | 0 | 0 |  |  |  |  |  |  |  |  |
| 29 | v-Myc | 0 | 0 | 1 |  |  |  |  |  |  |  |  |
| 30 | Suz12 | 0 | 0 | 0 |  |  |  |  |  |  |  |  |
| 31 | ZFP217 | 0 | 0 | 1 |  |  |  |  |  |  |  |  |
| 32 | Id4 | 0 | 0 | 1 |  |  |  |  |  |  |  |  |
| 33 | Rex | 1 | 0 | 1 |  |  |  |  |  |  |  |  |

METHODS AND VECTORS FOR CELL IMMORTALISATION

CROSS-REFERENCE TO RELATED APPLICATIONS

This is a national phase application, filed pursuant to 35 U.S.C. §371, of PCT application No. PCT/EP2011/005528, filed on Nov. 2, 2011, which claims the benefit of U.S. provisional application No. 61/409,503, filed on Nov. 2, 2010, and European patent application No. 10 014 200.9, filed on Nov. 2, 2010. The prior applications are incorporated herein by reference in their entireties.

The present invention relates to a method and to vectors for the immortalisation of cells independent of their type. It further relates to a cell or a cell line produced with the method or the vectors of the invention. The invention also relates to the use of this cell or cell line in in vitro applications and in the treatment of disease.

BACKGROUND OF THE INVENTION

Cell lines are used in basic research as well as in applied disciplines like protein production, drug discovery and toxicity testing and are also used for therapy in regenerative medicine approaches. The problem of existing cellular models is that they are either lacking biological relevance or the cells are not available in sufficient amounts. However, the elucidation of molecular processes heavily depends on suitable cell lines. Therefore, cells reflecting in vivo properties which can be produced in sufficient amounts are of high interest for modern life sciences.

Basically, cells can be derived from two different sources: they can be isolated as primary cells from individuals/animals, or they are provided by cell lines. The advantage of primary cells is that they closely reflect the properties of cells in vivo. This high biological relevance is unfortunately linked with several drawbacks like tedious and time consuming isolation procedures, a high batch to batch variability and complex cultivation conditions. The major limitation which hinders a more widespread use of primary cells is their limited proliferation capacity which significantly restricts expansion. Cell lines, on the other hand, are either isolated from tumours or generated upon spontaneous or induced immortalisation of primary cells. Cells of cell lines are unlimitedly available, homogeneous, show constant properties, are easy to handle and to maintain. However, so these cells lack many features and markers of tissue they were isolated from.

A major limitation of the establishment of new cell lines is (i) the unpredictability e.g. for spontaneous immortalisations of primary cell material, (ii) the fact that conventional immortalisation regimens solely with the help of known immortalising genes like the SV40 large T antigen (TAg) or viral oncogenes of the papilloma virus E6/E7 lead to the drastic alteration of the cell physiology. Therefore these cell lines do no longer reflect the physiology of the in vivo state and therefore the biological relevance is missing in these cell systems (iii) no system exists that is universal, meaning there is no single immortalising gene that is capable of establishing cell lines from any cell type, from different donors, and from different species.

Spontaneous immortalisation can occur from primary cell material derived from a tumour or in rare cases also from non-malignant or benign primary cells. These cell lines are easily maintained and expanded until a robustly proliferating cell line is established. The overall success rate of this process is low and therefore huge amounts of primary cell material have to be available. Due to the random nature of this process the properties of the resulting cell lines cannot be influenced and the resulting cell line mostly does not appropriately reflect its origin.

Conventional immortalisation regimens usually employ the recombinant expression of oncogenes like e.g. the catalytic subunit of the human telomerase (hTert), SV40 large T antigen (TAg), the polycomb protein Bmi1 or viral oncogenes E6/E7 from the human papilloma virus, the viral oncogenes E1A/E1B. A frequently used immortalisation gene is the hTert, which has proven useful for the expansion of a wide variety of cell types (Bodnar A G, Ouellette M, Frolkis M, et al. Science. Jan. 16, 1998; 279 (5349):349-352.). It acts by maintaining the ends of the telomeres. Telomeres are stretches of repetitive DNA at the very end of the linear chromosomes. These stretches cannot be replicated by DNA polymerases during replication and therefore the telomeres progressively shorten with every replication round. This "end-replication problem" can be overcome by the recombinant expression of hTert which eventually can lead to immortalisation. Cell types expanded and used for tissue engineering include e.g. bovine adrenocortical cells (reference), human dermal endothelial cells (Yang J et al., Nat Biotechnol. March 2001; 19(3):219-224) and human mesenchymal stem cells (Simonsen J L et al., Nat Biotechnol. June 2002; 20(6):592-596).

However, prolonged constitutive expression of telomerase induces changes in gene expression that lead to a premalignant phenotype (Milyaysky M, et al., Cancer Res. Nov. 1, 2003; 63(21):7147-7157). In addition, the use of hTert is restricted to certain human cell types as others need the concerted action of several genes for efficient immortalisation (Kiyono T et al., Nature. Nov. 5, 1998; 396(6706):84-88). Furthermore, human cells require different immortalisation strategies to cells from other mammals like e.g. murine cells (Rangarajan, A., et al., Cancer Cell, August; 6 (2):171-83, 2004). This leads to the fact that hTert fails in the establishment of murine cell line. Another gene that has been frequently used for immortalisation is TAg. TAg is a viral oncogene that is known to modulate the activity of a number of proteins. Among those, p53 and pRb are regarded as the most important ones for immortalisation. Binding of TAg to p53 inhibits p53 mediated growth control. However, the inactivation of p53 also leads to the interference with the DNA damage response which in turn leads to DNA damage of host cell chromosomes. TAg also interferes with the pRb (retinoblastoma protein) tumour suppressor. Through this interaction/inhibition the transcription factor E2F is activated, which is responsible for the progression of the cell through the cell cycle. However, TAg can only be employed for the establishment of rodent cell lines. For the immortalisation of human cells (i) TAg alone is not sufficient and therefore a second oncogene has to be used which is usually hTert and (ii) the resulting cell lines are often characterized by a grossly altered karyotype which is most probably due to the inactivation of the p53-driven DNA damage response.

Other genes that facilitate immortalization are the E6 and E7 proteins from the human papillomavirus. They interfere with cell cycle control and the regulation of apoptosis. E7 inhibits by binding to the pRB family members their function and thereby facilitates cell cycle progression as the cells enter the S phase by disrupting pRb-E2F complexes. E6 on the other hand is known to promote the degradation of p53 and thereby to disrupt the growth control by p53. Another function of E6 is the induction of telomerase activity which supports the immortalization of cells by maintaining telomere length. For the immortalisation of human cells both proteins—E6 and E7—are required. However, the combination of these genes works mainly for the immortalisation of epithelial cells. Another drawback is that these genes induce genomic instability so that the established cell lines are polyploid.

Other oncogenes seem to be cell type specific as they only work for a very limited number of cell types of certain species, for examples HoxA9/HoxB9 for murine macrophages (Wang et al., Nat Methods. 2006 April; 3(4):287-93.). Other examples are (i) the v-myc oncogene which allows the immortalization of murine/rodent macrophages (Pirami et al., Proc Natl Acad Sci U.S.A. 1991 Sep. 1; 88(17):7543-7.), (ii) the Epstein Barr Virus which readily immortalizes human B lymphocytes (Henle et al., Science. 1967 Sep. 1; 157(792):1064-5.) or (iii) the Polyoma middle T antigen which establishes murine embryonic endothelial cells (Williams et al., Cell. 1989 Jun. 16; 57(6):1053-63.)

In summary such conventional immortalization techniques very often lead to drastically altered or mutated cell lines. To circumvent this issue approaches were undertaken in which the effects of the immortalization genes are controllable. For example in WO 2010/000491 A1 at least two immortalizing genes are put under the control of a transcriptional regulation. In this setting the immortalizing genes are introduced into the primary cells and activated through an external stimulus which leads to the immortalization of the respective primary cells. The withdrawal of the external stimulus leads in turn to the inactivation of the immortalizing genes. This step efficiently induces in these immortalized cell lines a senescent phenotype—a cellular state which is characterized by a complete growth arrest and which is a tumor suppressor mechanism. Therefore the technology described in WO 2010/000491 A1 generates cell lines which are only useful for a very specialized field of research.

Thus, there is still a need in the art for a species and cell-type independent method for producing cell lines from a variety of primary cells.

SUMMARY OF THE INVENTION

The present invention relates to a method for immortalising cells with a finite life span, comprising the following steps:
(i) providing cells with a finite life span,
(ii) providing to said cells at least one gene, gene product or functional replacement thereof, from each of at least two of the following categories:
  (a) a gene or a gene product or functional replacement thereof which facilitates activation of BMP signalling,
  (b) a gene or gene product or functional replacement thereof, which is involved in maintaining pluripotency, or
  (c) a gene or gene product or functional replacement thereof, which facilitates the progression of the cell cycle,
and optionally one or more genes or gene products facilitating the selection of transduced cells.

Also, it relates to a cell or cell line producible with this method. Furthermore, the present invention relates to a vector comprising at least one expression cassette comprising expression control sequences operably linked to at least one gene or a set of vectors each comprising at least one expression cassette comprising expression control sequences operably linked to at least one gene, wherein the vector or set of vectors direct expression of at least two genes each selected from one of the following categories:

(a) a gene or a gene product or functional replacement thereof which facilitates activation of BMP signalling,
(b) a gene or functional replacement thereof, which is involved in maintaining pluripotency, or
(c) a gene or functional replacement thereof, which facilitates the progression of the cell cycle,
and optionally one or more genes or gene products facilitating the selection of transduced cells.

The invention also relates to the use of said cell or cell line or said vector or set of vectors for cellular assays, e.g. testing the response of cells to a compound, the establishment of a 3d cell culture model tissue engineering, for co-culturing with cells of one or more different cell lines, and/or cell encapsulation. Moreover, it relates to said cell or cell line or said vector or set of vectors for use in treating or preventing a degenerative disease, organ or cell damage/malfunction, an infectious disease, conditions related to the immune system, cancer, a psychological condition, or obesity.

This summary of the invention does not necessarily describe all features of the invention.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integer or step.

As used in this specification and the appended claims, the singular forms "a", "an", and "the" include plural referents, unless the content clearly dictates otherwise.

The present invention relates to a method for immortalising cells with a finite life span, comprising the following steps:
(i) providing cells with a finite life span,
(ii) providing to said cells at least one gene, gene product or functional replacement thereof, from each of at least two of the following categories:
   (a) a gene or a gene product or functional replacement thereof which facilitates activation of BMP signalling,
   (b) a gene or gene product or functional replacement thereof, which is involved in maintaining pluripotency, or
   (c) a gene or gene product or functional replacement thereof, which facilitates the progression of the cell cycle,
   and optionally one or more genes or gene products facilitating the selection of transduced cells.

In a preferred embodiment, said method further comprises after step (ii) an optional step (iii) of terminating or slowing down proliferation, inducing senescence and/or inducing differentiation in the immortalised cells. Preferably, this is achieved by partial or complete silencing, inactivation, and/or removal of said genes or gene products or functional equivalents thereof, for example using a DNA recombinase like the cre recombinase (Salmon et al., Mol Ther. 2000 October; 2(4):404-14 or a promoter system, which can be switched on and off by, e.g. by tetracycline as the TetON® or TetOFF® system.

The term "cells with a finite life span" refers to non-dividing cells, i.e. cells which do not divide during their life-time, and/or to slowly dividing cells, i.e. cells which in their organism of origin do not have the main or sole purpose of producing other cells by cell division and/or cells which senesce, i.e primary cells, which go through a limited number of cell divisions after isolation from a tissue to stop dividing and/or cells which go into apoptosis i.e primary cells, which directly go into apoptosis after isolation from a tissue or which go through a limited number of cell divisions after isolation from a tissue before going into apoptosis. The term, thus, excludes embryonic stem cells. In a preferred embodiment, it refers to cells derived from the ectoderm, endoderm or mesoderm lineage. Said cells can be growth-arrested cells (e.g. cells which are blocked at various stages of the cell cycle, i.e. G0, G1, S, G2, prophase, prometaphase and metaphase), non-proliferating cells, post- or non-mitotic cells, resting cells, benign cells, senescent cells, in vitro differentiated embryonic stem cells, in vitro differentiated induced pluripotent stem cells, terminally differentiated cells, and preferably primary cells. Preferred cells are cells selected from the group consisting of adipocytes, adult stem cells, astrocytes, B-cells, cardiomyocytes, chondrocytes, cornea epithelial cells, dendritic cells, endocrine cells, endothelial cells, epithelial cells, fibroblasts, glia cells, granulocytes, hematopoietic cells, hematopoietic stem cells, hepatocytes, keratinocytes, intestinal epithelial cells, liver cells, lung epithelial cells type I, lung epithelial cells type II, lymphocytes, macrophages, mammary epithelial cells, melanocytes, mesangial cells, mesenchymal stem cells, muscle cells, myoblast, natural killer cells, neuronal cells, neuronal stem cells, neutrophiles, osteoblasts, pancreatic beta cells, pericytes, preadipocytes, progenitor cells, prostate epithelial cells, renal epithelial cells, renal proximal tubule cells, retinal pigment epithelial cells, sertoli cells, skeletal muscle cells, smooth muscle cells, stem cells, stroma cells, T-cells and subsets of said cell types. Said cells are non-mammalian cells (e.g. from fish or bird species) or mammalian cells (e.g. from mice, rats, monkeys, pigs, dogs, cats, cows, sheep, goats), preferably human cells.

In a preferred aspect of the invention, said cells with a finite life-span are derived from an individual or a group of individuals with a specific genetic background, e.g. disease related, known to lead to a specific response to medical treatments, wherein the specific genetic background preferably differs from the wild-type by at least one mutation, deletion, duplication, SNP-related variation, and/or chromosome aberration. Among the genes that might be altered by one of the mentioned mechanisms are those genes that are relevant for drug metabolism. This includes the different isoforms of the cytochrome P450 enzymes like, for example, the isoforms CYP2D6, CYP2C8, CYP2C9, CYP2C19, CYP1A1, CYP3A4, CYP3A5, CYP2A6, CYP2B6, CYP2E1.

Other possible affected genes are the ones involved in drug transport like the transporters from the adenosine triphosphate (ATP)-binding cassette (ABC) family. There are a total of 48 known ABC genes, with ABCB1 (P-glycoprotein, multidrug resistance [MDR] 1), ABCC1 (MRP1), ABCG2 (BCRP, MXR, ABCP), and ABCC2 (MRP2) as the most prominent ones. In addition, uptake transporters like the organic anion transporting proteins (OATPs) e.g. OATP1B1 and OATP1B3 can be altered in their function by the abovementioned mechanisms.

Such dependence on the genetic background is also known for other genes involved in drug metabolism like e.g. the thiopurine s-methyltransferase (TPMT), the N-acetyltransferase 2 (NAT2), the UDP glucuronosyltransferase 1 family polypeptide A1 (UGT1A1), and methylenetetrahydrofolate reductase (MTHFR), esterases, thiol methyltransferase, catechol-Omethyltransferase (COMT), glutathione-S-transferases, histamine methyltransferase, reductases, oxidases, aldehydehydrogenase, monoamine oxidase B, catalase, superoxide dismutase, trimethylamine N-oxidase, dihydropyrimidine dehydrogenase.

Furthermore, also the therapeutic response can be genotype specific. This stems from the fact that the expression of disease related target genes like e.g. G-protein coupled receptors, ion channels, kinases or enzymes can be modulated by mutation like e.g. single nucleotide polymorphism. An example is Alzheimer Disease in which the variants of apolipoprotein E (APOE) determine the risk of developing Alzheimer Disease. The APOE-4 allele is associated with the risk of developing Alzheimer Disease whereas the APOE-2 allele seems to protect from Alzheimer Disease. Another example is the Angiotensin I-converting enzyme ACE which is the target of the ACE inhibitor family of drugs (captopril, enalapril) currently used as antihypertensive agents. These ACE-related polymorphic variants have been associated with indications like hypertension, atherosclerosis, stroke, left ventricular hypertrophy, susceptibility to myocardial infarction, diabetic nephropathy, Alzheimer Disease. Also for asthma several drug response pathways have been identified that are influenced by the genotype. Amongst them are drugs that target the glucocorticoid receptor (Beclomethasone), the β2-adrenergic receptor (Albuterol), the 5-lipoxygenase enzyme (zileuton), cystein leukotriene 1 receptor antagonists (zafirlukast) or the muscarinic receptor 3 (Ipratropium).

In cancer several genes like thiopurine methyltransferase (TPMT) or dihydropyrimidine dehydrogenase are involved in metabolizing anticancer agents. Cancer highlights also the fact that one organism can harbour different genetic variants of a given gene. These differences emerge when the cancer cells are compared to the non-malignant cells. Such differences can be used for a targeted therapy examples of such genetic variants are human epidermal growth factor receptor 2, the fusion protein BCR-ABL, BRCA1, BRCA2 or K-ras.

The term "immortalising cells" refers to conferring to one or more cells the ability to divide or proliferate to an extent which exceeds its natural, i.e. original proliferation capability, for example within its organism of origin or if isolated and maintained in cell culture. In a preferred embodiment, said cell acquires the ability to divide or proliferate indefinitely. The term "immortalised cells" also includes post-immortalised cells, i.e. cells which have been immortalised with the method of the invention, but in which proliferation has been terminated or slowed down and/or in which senescence and/or differentiation has been induced according to above-described optional step (iii) of said method. Accordingly, instead of "immortalising cells", the term "expanding cells" may alternatively be used. Immortalised cells within the meaning of the present invention are not transformed cells, i.e. they are not tumorigenic. Immortalised cells are preferably non-tumorigenic, wherein non-tumorigenic cells preferably are cells which exhibit at least one, two or all three of the following characteristics: (i) do not grow in soft agar, (ii) do exhibit contact-inhibition, and/or (iii) do not cause tumour growth in immunocompromised mice, like SCID mice, RAG2γc mice or nude mice. More preferably, said immortalised cells essentially retain the differentiation-specific physiological properties of said cells with a finite life span on which the immortalized cells are based. Essentially retaining the differentiation-specific physiological properties means that the cell or cell line retains at least one property of the cell with a finite life-span which is to be investigated using the immortalised cells. Primarily, this will be related to the primary function(s) of the cell with a finite life-span. Said properties obviously depend on the cell-type and next to the following non-limiting examples, the person skilled in the art can only be referred to methods for examining cell properties known in the art. Immortalized endothelial cell lines that retain at least one property of the endothelial cell on which they are based can be characterised by comparing to the originator cells (i.e. the cells with a finite life-span) the expression of one or more of the following markers CD31 (Pecam-1), Tie2, VEGFR1, VEGFR2 (CD309), CD105, von Willebrand factor, and coagulation factor VIII, preferably CD31, CD105. Further, the endothelial cells can be characterised by the inducible expression of CD54 (ICAM1), CD62E (E-Selectin), and CD106 (VCAM). This induction can be achieved by, e.g. TNFα. The endothelial cell lines can also be characterized by functional assays, which detect the activity of the endothelial NO synthase (eNOS), which detect the uptake of the acetylated form of low density lipoprotein (acLDL), or which demonstrate that the cell lines form tube-like structures on extracellular matrices (e.g. matrigel). In addition, the endothelial cell lines can be characterized by the formation of blood vessels after transplantation, e.g. in immunocompromised mice.

Immortalized chondrocyte cell lines can be characterized by the expression of the transcription factor Sox9 or Sox10. In addition, the chondrocyte cell lines can be characterized by the production of extracellular proteins like e.g. different collagens (collagen I, collagen II, collagen X), proteoglycan, or chondroitin 4-sulfat.

Immortalized epithelial cell lines, e.g. epithelial cells from the lung, keratinocytes, the intestine or the kidney can be functionally characterized by the production of the transepithelial electric resistance (TEER) with values above 50Ω per $cm^2$. In addition or alternatively, epithelial cells can be functionally characterized by assaying the permeability of substances through a monolayer of the respective epithelial cells. In addition or alternatively, epithelial cells can also be characterized by efflux transporter like e.g. p-glycoprotein, multidrug resistance gene 1a (Mdr1a), multidrug resistance associated protein (MRP) 1, MRP2, MRP4, MRP5, or ATP-binding cassette subfamily G member 2 (ABCG2). Neuronal cell lines can be characterized by the expression of βIII-tubulin, tyrosine hydroxylase, aromatic L-amino acid decarboxylase (AADC), dopamine transporter (DAT), choline O-acetyltransferase (ChAT), LIM homeobox transcription factor 1, beta (LMX1B), and microtubule-associated protein 2 (MAP2). The neuronal cells can also be characterized by measuring the action potential. Established cardiomyocytes lines can be functionally characterized by spontaneous beating. In addition, they also express troponin T type 2 (cardiac) (TnTc), myocyte enhancer factor 2C (MEF2C), myosin, light chain 7, regulatory (MYL2A), myosin, heavy chain 7, cardiac muscle, beta (MYH7), or NK2 transcription factor related, locus 5 (NKX2.5). Established hepatocytes can be characterized by the expression of albumin, alpha fetoprotein (AFP), hepatocyte nuclear factor 4, alpha (HNF4a), Cytokeratin 18 (CK18), Sox17, CCAAT/enhancer binding protein (C/EPBa), alpha-1-antitrypsin, or Mrp2. In addition, hepatocyte cell lines can be functionally characterized by measuring the activity of phase I components of the drug metabolism (through one of the cytochrom p450s, e.g. CYP1A2, CYP2A6, CYP2C19, CYP2D6, CYP2B6, CYP2C8, CYP2C9, CYP3A4, or CYP2E1) and phase II components of the drug metabolism (e.g. through UDP-Glucuronosyltransferase, Glutathione S-transferase, Sulfotransferase, N-acetyltransferase, or Amino acid N-acyl transferase) or bile export through the ATP-binding cassette, sub-family B (MDR/TAP), member 11 (ABCB11). Cell lines established from pancreatic beta cells can be characterized by the expression of ISL LIM homeobox 1 (Isl-1), Pax 6, Nkx 6.1, Pdx-1, prohormone convertase 1/3, or prohormone convertase 2. They can be functionally characterized by the secretion of insulin in response to glucose. T-lymphocytes cell lines can be characterized by the expression of CD3, CD4, CD8, CD25, CD28, or the T-cell receptor. They can be functionally characterized by measuring the release of cytotoxins like perforin, granzymes, and granulysin. B-lymphocyte cell lines can be characterized by the expression of CD19, CD20, or the IL7 receptor. In addition, they can be functionally characterized by the production of antibodies. Cell lines established from mesenchymal stem cells can be characterized by the expression of CD73, CD105, or CD271. They can be functionally characterized by their ability to differentiate into osteoblasts, adipocytes, or chondrocytes. Cell lines established from hematopoetic stem cells or hematopoetic progenitor cells can be characterized by the expression of c-kit, Sca1, CD34, CD150, CD48, or CD244. They can be functionally characterized by their ability to differentiate into all kind of blood cell types like myeloid (monocytes, macrophages, neutrophils, basophils, eosinophils, erythrocytes, megakaryocytes/platelets, or dendritic cells), and lymphoid cells (T-cells, B-cells, or NK-cells). In addition, they can be functionally charaterized by their ability to form colonies (CFU—colony forming units) in vitro. They can also be characterized by their ability to rescue an individual (e.g. mice) after irradiation or other treatments e.g. cyclophosphamide which destroy the host bone marrow.

Accordingly, the present invention also relates to a cell or cell line producible with the method of the invention. Preferably, said cells comprise at least one gene, gene product or functional replacement thereof, from each of at least two of the following categories:
(a) a gene or a gene product or functional replacement thereof which facilitates activation of BMP signalling,
(b) a gene or gene product or functional replacement thereof, which is involved in maintaining pluripotency, or
(c) a gene or gene product or functional replacement thereof, which facilitates the progression of the cell cycle,
and optionally one or more genes or gene products facilitating the selection of transduced cells.

The present invention also relates to a vector comprising at least one expression cassette comprising expression control sequences operably linked to at least one gene or a set of vectors each comprising at least one expression cassette comprising expression control sequences operably linked to at least one gene, wherein the vector or set of vectors direct expression of at least two genes each selected from one of the following categories:
(a) a gene or a gene product or functional replacement thereof which facilitates activation of BMP signalling,
(b) a gene or functional replacement thereof, which is involved in maintaining pluripotency, or
(c) a gene or functional replacement thereof, which facilitates the progression of the cell cycle
and optionally one or more genes or gene products facilitating the selection of transduced cells.

The term "operably linked" means that a recombinant gene or coding sequence and one or more expression control sequences are connected in such a way as to permit expression of the nucleic acid sequence when introduced into a cell, wherein the time and amount of expression depends on the expression control sequences. The term "expression cassette" refers to a nucleotide sequence capable of expressing a recombinant gene or coding sequence. An expression cassette comprises one or more expression control sequences operably linked to one or more recombinant genes or coding sequences so as to achieve expression of the protein product encoded by a gene or coding sequence in a cell or to achieve expression of RNA molecules, e.g. RNA molecules that act as regulators like miRNAs. Preferably, at least two or three genes selected from each one of above categories are comprised on one vector, preferably under the control of one expression control sequence. In the later embodiment it is preferred that the at least two or three genes are transcribed as one mRNA but are translated independently. This may be achieved by the introduction of so-called internal ribosome entry sites (IRES).

In various embodiments, said vectors are viral, preferably retroviral, more preferably lentiviral vectors, adenoviral vectors, or adeno-associated viruses; non-viral, preferably plasmids, bacterial artificial chromosomes or cosmids; and/or non-integrating vectors like episomal vectors, minicircles or non-integrating retroviral or lentiviral vectors. In a further embodiment, said expression cassettes comprise a system allowing for removal, regulating or silencing of the genes comprised therein. Examples for such systems are the use of DNA modifying enzymes like the cre recombinase (Salmon et al., Mol Ther. 2000 October; 2(4):404-14), the Flp recombinase, the Phi31 integrase, meganucleases or engineered zinc finger nucleases, or the use of transcriptional regulation systems like the Tet-system, the T-Rex system, the AIR-system, the erythromycin system, the PIP system, the Rheo-switch system, the cumate system, the coumermycin system, the NICE system.

The vectors comprising the expression cassettes can be introduced into cells by transduction methods known in the art, for example plasmid transduction which can be e.g. achieved by electroporation, calcium phosphate transfection or lipofection or by cell infection with viral vectors. The expression cassette may or may not be integrated into the chromosome or may be present extra chromosomally, e.g. as a minicircle or in other episomal forms which can be maintained by, e.g., the Epstein-Barr virus nuclear antigen (EBNA) or the SV40 large T antigen. Another example is the delivery of extra chromosomally expression cassettes which are delivered by viruses like adenoviruses.

Referring to both the above-described method, a cell or cell line produced therewith and said vector or set of vectors, said genes or gene products are, in one embodiment, cellular genes or gene products. Also, it is preferred that at least one gene, gene product or functional replacement thereof is from category (a), i.e. combination of category (a) and (b) as well as category (a) and (c) are particularly preferred. It is even more preferred that at least one gene, gene product or functional replacement thereof is from each of category (a), (b) and (c).

The term "gene which facilitates activation of BMP signalling" refers to a gene encoding a gene product, which induces signalling through the BMP type I receptors (BMPR-I) to which e.g. the BMPR-IA (ALK3) and the BMPR-IB (ALK6) belong. These receptors can e.g. be activated through endogenous ligands like BMP2 or BMP4. Downstream signalling of the BMPR-I receptors activate R-SMAD proteins. SMAD1, SMAD5 and SMAD8 are the R-SMADs of the BMP-signalling which form a complex with common partner SMAD (co-SMAD; SMAD4). This complex of R-SMADs and co-SMAD then translocates into the nucleus to regulate transcription of target genes (Miyazono et al., J Biochem. 2010 January; 147(1):35-51.). Accordingly, the term "gene product which facilitates the activation of the BMP signalling" refers to the encoded protein. Preferred examples of such genes code for members of the inhibitor of DNA binding (Id) family, which are transcriptional regulators that contain a helix-loop-helix (HLH) domain but not a basic domain. These proteins are, thus, dominant negative helix-loop-helix protein. The term "functional replacement thereof" in the context of genes, which facilitate the activation of the BMP signalling, refers to genes encoding BMP2, BMP4, ALK3, ALK6, SMAD1, SMAD5, SMAD8. Preferably, the term "functional replacements of Id genes or Id proteins" are genes or the encoded proteins, which regulates the expression of an Id gene family member. Said Id family member is preferably selected from the group consisting of Id1, Id2, Id3 and Id4. Functional replacements of Id gene family members are preferably genes upregulating one or more Id gene family members. Id family members are upregulated, for example, by genes that are involved in the beta-catenin/T cell factor (TCF) signalling pathway, the bone morphogenetic proteins signalling (BMP), the Erk/MAPK signalling pathway, the mammalian target of rapamycin (mTOR) pathway, the fibroblast growth factor (FGF)-2 signalling, the JAK2-STAT5 signalling, activin, HiF-1, h-ras, Sp1, AP-1, E2F1, Pax3, Pax7, n-Myc or c-Myc. In addition, Id gene family members are upregulated by a mutated p53 pathway.

The term "gene involved in maintaining pluripotency" refers to gene encoding a gene product, which is either involved (i) in the pluripotency circuit (Loh et al., Cell Cycle. 2008 Apr. 1; 7(7):885-91. Molecular framework underlying pluripotency.) and/or (ii) in the reprogramming of somatic cells (Maherali and Hochedlinger, Cell Stem Cell. 2008 Dec. 4; 3(6):595-605. Guidelines and techniques for the generation of induced pluripotent stem cells.). Accordingly, the term "gene product involved in maintaining pluripotency" refers to the encoded protein. In a preferred embodiment, said gene or gene product which is involved in maintaining pluripotency is selected from the group consisting of Nanog, Sox1, Sox2, Sox3, Klf1, Klf2, Klf4, Klf5, Esrrb, Lin28, the miR290 cluster, Ecat1, Dppa5, ERas, Ecat8, Gdf3, Dppa4, Dppa2, Sall4, Oct3/4, Utf1, Tcl1, and Dppa3. Preferred examples of such gene products are transcriptional regulators whose target genes are involved in maintaining pluripotency. Preferred members of this group comprise Nanog, Sox1, Sox2, Sox3, Klf1, Klf2, Klf4, Klf5, Esrrb, Dppa4, Dppa2, Sall4, Oct3/4, and Utf1. It is preferred that the selection comprises Nanog, Klf4, and/or Sox2, more preferably Nanog; Sox2; or Nanog and Sox2. Alternatively, Klf4 is particularly preferred.

The term "gene product, which facilitates progression of the cell cycle" refers to a gene which facilitates progression through one of the cell cycle phases: G1/G0-Phase, S-Phase, G2-Phase and M-Phase (The Cell, 2nd edition, A Molecular Approach, by Geoffrey M Cooper. Boston University, Sunderland (Mass.): Sinauer Associates; 2000). Preferably, such a gene encodes a gene product which acts through the inactivation of at least one of the tumor suppressor genes p53, p21, pRB, p16Ink4a, p19ARF, p14ARF or p27 or the encoded proteins. Preferably, said gene or gene product which facilitates cell cycle progression directly or indirectly activates at least one cyclin or inhibits the repression thereof In a preferred embodiment the cell cycle progression facilitating gene is of cellular or viral origin. Preferred examples of cell cycle progression facilitating gene of cellular origin and selected from the group consisting of Fos, Jun, Myc, n-myc, h-ras, raf, k-ras, RhoA, Rac1, Rac2, Rac3, Myb, beta-catenin, Lmo2, Mdm2, Pim1, Pim2, Yap1, Gli1, Gli2, Gli3, E2F1, E2F2, E2F3, cyclin A, cyclin b, cyclin d, Suz12, Tbx2, Tbx3, Ezh2, Bmi1, Cbx7 and Rex, and wherein said selection preferably comprises Fos, Myc, RhoA, Myb, beta-catenin, Lmo2, Yap1, Suz12 Ezh2, Bmi1, and/or Rex, more preferably Fos, Myc, and/or Ezh2. Preferred examples of cell cycle progression facilitating gene is of viral origin is selected from the group consisting of E7, Core, E1a, E1b, E6, vGPCR, Sv40 large T antigen, and wherein said selection preferably comprises E7, Core, E6 and/or Sv40 large T antigen, more preferably E7 and core.

In each case it is preferred that the mammalian, more preferably human, ape or rodent homolog of the respectively indicated gene is used unless the protein referred to is a viral protein as, e.g. E7 or Sv40 large T antigen. Comprised are variants of the indicated genes, which retain the respective ability of gene according to categories (a), (b) and/or (c) and the protein encoded by the respective gene share at least 70%, 75%, 80%, 81%, 82%, 83%, 84%, 85%, 86%, 87%, 88%, 98%, 90%, 91%, 92%, 93%, 94%, 95%, 96%, 97%, 98%, 99% or even 100% amino acid identity with the human, mouse or viral protein encoded by the gene respectively indicated in Table 1 below. Preferably, the level of identity is determined over the entire length of the respective reference protein.

In a particularly preferred embodiment, said cell cycle progression facilitating gene or gene product is selected from the group consisting of Fos, E7, Ezh2, and Myc, most preferably Myc said gene or gene product involved in maintaining pluripotency is selected from the group consisting of Nanog and Sox2, and said Id family member is selected from the group consisting of Id1, Id2, Id3, and Id4.

In another embodiment, one or more further genes selected from the group consisting of Bcl-2, Bcl-X1, HoxB4, Tlx1, vGPCR, HoxA9, Hoxb8, Stat3, ZFP217 are expressed in said cells, wherein said selection preferably comprises Bcl-2, HoxA9, and/or ZFP217.

Particularly, preferred combinations comprise at least: (a) Id1, Id2, Id3 or Id4, preferably Id2; (b) Nanog and; (c) EZH2; or (a) Id1, Id2, Id3 or Id4, preferably Id2; (b) Nanog and; (c) Fos; (a) Id1, Id2, Id3 or Id4, preferably Id2; (b) Nanog and; (c) Myc; (a) Id1, Id2, Id3 or Id4, preferably Id2; (b) Nanog and; (c) E7; (a) Id1, Id2, Id3 or Id4, preferably Id2; (b) Sox2 and; (c) EZH2; or (a) Id1, Id2, Id3 or Id4, preferably Id2; (b) Sox2 and; (c) Fos; (a) Id1, Id2, Id3 or Id4, preferably Id2; (b) Sox2 and; (c) Myc; (a) Id1, Id2, Id3 or Id4, preferably Id2; (b) Sox2 and; (c) E7; (a) Id1, Id2, Id3 or Id4, preferably Id2; (b) Klf4 and; (c) EZH2; or (a) Id1, Id2, Id3 or Id4, preferably Id2; (b) Klf4 and; (c) Fos; (a) Id1, Id2, Id3 or Id4, preferably Id2; (b) Klf4 and; (c) Myc; (a) Id1, Id2, Id3 or Id4, preferably Id2; (b) Klf4 and; (c) E7.

Further preferred gene combinations of categories a), b) and/or c) comprise or consist of the following gene combinations:

Id2, Fos, TAg, Id3, E7, Bcl2, Core, Id1, Myc, Lmo2, Yap1, Nanog, Sox2, Ezh2, and Rex;
(ii) Id3, E7, Core, Id1, Myc, Lmo2, Yap1, Nanog, Ezh2, and Rex;
(iii) core, Id1, Lmo2, and Nanog;
(iv) RhoA, and Ezh2;
(v) Id2, Fos, Id3, E7, core, Id1, and Myc;
(vi) E7, and Myc;
(vii) Myb, E7, HoxA9, Core, and Myc;
(vii) Id2, Fos, βcat, TAg, Id3, E7, E6, HoxA9, Bmi1, core, Klf4, Id1, Myc, Lmo2, and Nanog,
(viii) Sox2, RhoA, Ezh2, and Rex;
(ix) Id2, Fos, Id3, core, Klf4, Id1, Nanog, Ezh2, and Id4;
(x) Id2, Fos, and Id3;
(xi) Klf4, Id1, Lmo2, Yap1, and Nanog;
(xii) Sox2, Ezh2, Rex;
(xiii) Id2, Fos, Myb, Id3, E7, Id1, Myc, Nanog, Ezh2, and Rex;
(xiv) Fos, Id3, Bmi1, Yap1, and Nanog;
(xv) Id2, Fos, and Id3;
(xvi) Suz12, Id4, and Rex;
(xvii) Id2, Fos, βcat, TAg, E7, E6, Id1, and Myc;
(xviii) Id2, Fos, Id1, and Myc;
(xix) Id2, Id1, and Myc;
(xx) Id2, Fos, and Id1;
(xxi) Fos, Id1, and Myc;
(xxii) Id2, Fos, Myc;
(xxiii) Id2, Fos, Myb, Id3, and Bcl2;
(xxiv) Id2, Fos, Id3, HoxA9, Id1, Nanog, and Ezh2;
(xxv) Id1, Id3, Fos, Ezh2, and Nanog;
(xxvi) E7, HoxA9, Sox2, and Ezh2;
(xxvii) Id1, Id3, Fos, TAg, E7, HoxA9, Nanog, Sox2, and Ezh2;
(xxviii) TAg, Id3, E7, E6, Lmo2, Nanog, Ezh2, and ZFP217;
(xxxix) Id2, TAg, E7, and Myc;
(xxx) Fos, βcat, TAg, E7, Id1, and Myc;
(xxxi) Id2, Fos, TAg, E7, and Myc;
(xxxii) Id2, Fos, Id3, E7, core, Klf4, Id1, Lmo2, Nanog, Sox2, and Ezh2;
(xxxiii) Fos, Nanog, and Ezh2;
(xxxiv) Id2, Fos, TAg, Id3, core, Id1, Lmo2, and Nanog;
(xxxv) Id3, E7, Id1, Lmo2, Yap1, Nanog, and Ezh2;
(xxxvi) Id2, Fos, Id1, and Ezh2;

(xxxvii) Id2, Fos, E7, core, Lmo2, and Nanog;
(xxxviii) Id2, Fos, βcat, Id3, E7, Id1, Lmo2, and Ezh2;
(xxxix) Id2, E7, Nanog, and Ezh2;
(xl) Id2, Myb, Id3, E7, E6, Myc, Yap1, Nanog, and Ezh2;
(xli) Id2, Fos, Id3, E7, E6, core, Id1, Lmo2, Yap1, Nanog, Sox2, and Ezh2;
(xlii) Id2, Fos, E7, Id1, Lmo2, Yap1, Nanog, and Sox2;
(xliii) E7, E6, Bmi1, Id1, Myc, Lmo2, Yap1, Nanog, and Sox2;
(xliv) Id2, E7, Myc, Nanog, Sox2, and Ezh2
(xlv) Id2, Fos, Id3, E7, E6, Bcl2, HoxA9, Bmi1, Klf4, Id1, Myc, Nanog, Sox2, Ezh2, and Gli1
(xlvi) Fos, Id3, E7, Id1, Nanog, and Sox2
(xlvii) Id2, Fos, Id3, E7, HoxA9, Id1, Myc, Nanog, Sox2, Ezh2, and Gli1
(xlviii) Id3, HoxA9, Myc, and core
(xlix) Myb, Id3, core, and Myc
(l) Id3, Myc, Bcl2, Bmi1, and HoxA9
(li) PymT, Bcl2, Myc, Id3, and HoxA9
(lii) PymT, Myc, core, and βcat
(liii) Id1, and Myc
(liv) Id2, and Myc
(lv) Id3, and Myc
(lvi) Id4, and Myc
(lvii) βcat, and Myc
(lviii) βcat, and PymT, Myc
(lix) βcat, and Myc, Bmi1
(lx) Myc, BcL2, and βcat
(lxi) Myc, HoxA9, and ID3
(lxii) βcat, and Myc
(lxiii) core, Myc, and ID3.
(lxiv) Id3, core, Lmo2, and Ezh2
(lxv) Id3, E7, E6, Yap1, and Nanog
(lxvi) Myc, Klf4
(lxvii) Fos, E7, Klf4, Lmo2
(lxviii) TAg, Klf4
(lxix) TAg, core, Klf4
(lxx) Id3, Klf4, Id4
(lxxi) Fos, E7, Klf4
(lxxii) Fos, E7, Klf4, ID4
(lxxiii) TAg, core
(lxxiv) ID2, ID3, core
(lxxv) Bcl2, core, Myc, Rex
(lxxvi) Id3, Bcl2, core, Myc
(lxxvii) TAg, Myb, ID3, core, Myc
(lxxviii) ID2, Bcl2, core, Myc
(lxxix) TAg, ID3, Bcl2, core, Rex
(lxxx) TAg, E6, Bcl2, core, ID4, Rex
(lxxxi) TAg, ID3, Bcl2, core, Myc, Rex The "functional replacement" of a given gene or gene product refers inter alia to the knock-down or knock-out of another gene or gene product, wherein this other gene or gene product antagonizes the given gene or gene product. The gene or gene product knock-out can be achieved by all suitable methods known in the art, for example by zinc finger technology or by homologous recombination. The gene or gene product knock-down can for example be achieved by RNAi (e.g. siRNA, shRNAs or antisense oligonucleotide), miRNA technology, morpholinos, ribozymes and protein competition. Preferably, the protein competition is achieved by using antibodies specifically binding to the gene or gene product, which antagonizes the given gene or gene product, or by dominant negative mutants of the gene or gene product, which antagonizes the given gene or gene product. The functional replacement of a given gene or gene product can also be achieved by the addition of chemicals, e.g. low molecular weight molecules that lead to the activation of genes falling into one of the categories (a), (b) or (c) or inhibit or downregulate genes or gene products that antagonize the given gene or gene product of the categories (a), (b) and/or (c).

A gene or gene product facilitating the selection of transduced cells can be one which facilitates cell survival and/or division in an environment which is detrimental for cell survival and/or division or one which facilitates cell identification and/or separation. Preferably, said optional gene or gene product facilitating the selection of transduced cells is selected from the group consisting of antibiotics (e.g., chloramphenicol, blasticidin S, puromycin, histidinol, hygromycin B, neomycin, zeocin, Bleomycin), fluorescence markers (e.g. green fluorescent protein, red fluorescent proteins, yellow fluorescent protein, cyan fluorescent protein, far red fluorescent proteins like HcRed1), surface markers (e.g. truncated CD34, low nerve growth factor receptor), and genetically encoded tags (e.g. biotin tag, a halo tag, a snap tag) or enzymes that convert a non-fluorescent molecule into a fluorescent one (e.g. beta-galactosidase).

Generally, the expressions of all above-mentioned genes is constitutive, regulatable and/or inducible. The expression can, for example, be regulated by using appropriate promoters known in the art. For constitutive expression, known promoters of housekeeping genes or constitutive viral promoters are particularly suited. Examples include the constitutive viral CMV, SV40, RSV, MLV, and SFFV promoters. Examples for constitutive mammalian promoters are the PGK, ubiquitin, and EF1α promoter. Regulatable or inducible promoters, of which hundreds are known to the skilled person as well, are preferably induced by physical (e.g. light, temperature etc.) or biological/chemical (proteins, compounds etc.) factors.

For example, for regulatable/inducible expression, transcriptional regulation systems can be employed, e.g. a transcription regulation system based on a tet regulation system. The tet regulation system is known in the art, for example, described in Corbel, S. Y. et al. (2002, Curr. Opin. Biotechnol. 13: 448-452). Typically, the molecules Tetracycline or Doxocycline are used as the appropriate ligand for the tet system. Other transcription systems include but are not restricted to the AIR-system, the erythromycin system, the PIP system, the Rheoswitch system, the cumate system, the coumermycin system, the NICE system, and the T-Rex system. An additional variant of this regulation approach is fusing the transcriptional activator to domains that mediate dimerization and/or nuclear import upon binding of small molecules. Examples are the rapamycin regulation system, the fusion of biotin or the fusion of steroid binding domains to the transcriptional activator.

Other systems for the regulation of expression rely on the use of DNA modifying enzymes. In such a setting the expression cassette is flanked by recognition sites for the respective DNA modifying enzymes. Enzymes that can be used for such purposes include e.g. the cre recombinase, the Flp recombinase, the Phi31 integrase, meganucleases or engineered zinc finger nucleases.

Another system to regulate expression is fusing the respective gene to domains that facilitate binding to small molecules. An example for this approach is the estrogen binding domain.

Another method to regulate the function of the immortalizing genes is the controlled degradation of recombinant proteins. In this setting a destabilization domain is fused to the recombinant gene. When such construct is introduced in mammalian cells the gene is expressed but the protein is rapidly degraded. The addition of a small molecule which stabilizes the destabilization domain leads also to the stabilization of the respective recombinant protein. Several systems that allow this regulation on the protein level have been described e.g. in Iwamoto et al., Chem Biol. 2010 Sep. 24; 17(9):981-8 and Banaszynski et al., Cell. 2006 Sep. 8; 126(5):995-1004.

Regulatable or inducible gene expression is particularly useful in above-described optional step (iii) of the method of the invention. Gene expression can also be cell type specific, which can be achieved by cell type specific promoters or cell type specific enhancers or by a combination of both promoter and enhancer, for example the αMHC or the Myh6 promoter for cardiomyocytes, the tie2 promoter or the ICAM2 promoter for endothelial cells, CD11c promoter for dendritic cells, the albumin or the alpha1 antitrypsine or the alpha fetoprotein promoter for hepatocytes, the vilin or the cytokeratin18 promoter for intestinal epithelial cells, the tau or the nestin promoter for neuronal cells, or the insulin promoter for pancreatic beta cells.

In a preferred embodiment, said genes, gene products or functional equivalents are (i) provided only in a subset of the cells with a finite life span of step and/or (ii) expressed only in a subset of said cells. Therein, the subset of cells wherein said genes, gene products or functional equivalents are provided may be larger than the subset of cells wherein the same are expressed or produced One advantage of this embodiment is that a particularly cell type can be immortalised, which is not separated and/or separable from other cells, for example because cell numbers are too small, the cells of this type are physically attached to other cells (rendering separation inconvenient, difficult or impossible) or the cells are inaccessible by known means for cell separation. The principle underlying this embodiment is that one cell type among one or more other cell types divides faster than other cells and therefore outcompetes or outgrows said other cells, facilitating its isolation, which may have been inconvenient, difficult or impossible before immortalisation.

The present invention further relates to the use of the cell or cell line or the vector or set of vectors of the invention for cellular assays, e.g. testing the response of cells to a compound, the establishment of a 3d cell culture model, tissue engineering, for co-culturing with cells of one or more different cell lines, and/or cell encapsulation, i.e. (i) the protection of transplanted cells from immune rejection by an artificial, semipermeable membrane, potentially allowing transplantation (allo- or xenotransplantation) without the need for immunosuppression or (ii) allowing detoxification e.g. in response to acute liver failure or (iii) allowing metabolisation in diseases like diabetes.

The present invention also relates to the cell or cell line or the vector or set of vectors of the invention for use in treating or preventing a degenerative disease, organ or cell damage/malfunction (e.g. Amyotrophic Lateral Sclerosis (ALS), Alzheimer's Disease, Parkinson's Disease, Multiple system atrophy, Niemann Pick Disease, Atherosclerosis, Progressive Supranuclear Palsy, Cancer, Tay-Sachs Disease, Diabetes, Heart Disease, Keratoconus, Inflammatory Bowel Disease (IBD), Prostatitis, Osteoarthritis, Osteoporosis, Rheumatoid Arthritis, Huntingtons Disease, Liver Zirrhosis, age-related macular degeneration, acute liver failure, dementia, stroke, Chronic obstructive pulmonary disease (COPD), bone damage, anaemia, asthma, hypertension, epilepsy, chronic pain), an infectious disease (e.g. B, hepatitis C, HIV, influenza), conditions related to the immune system (e.g. graft-versus-host reactions, allergies, systemic lupus erythematosus, sepsis, multiple sclerosis, psoriasis), cancer, a psychological condition (e.g. trauma, depression, schizophrenia), or obesity.

BRIEF DESCRIPTION OF THE FIGURES

The following figures are merely illustrative of the present invention and should not be construed to limit the scope of the invention as indicated by the appended claims in any way.

FIG. 3: Digital code of immortalisation. Depicted are the infections that led to immortalisation of the respective cell types. The following abbreviations for the different cell types were used: human fibroblasts—human foreskin (d1/d2) and human adult dermal fibroblast; Human ost—human osteoblasts; chondro—human chondrocytes; human kera—human keratinocytes (foreskin d2/ad—adult d1); ma—bovine macrophages; stro—human bone marrow stroma cells (d1/d2/d3/d4/d5); lung—lung epithelial cells (d1/d2); fibroblast—murine ear fibroblasts; endothelial cells (juvenile)—human umbilical cord endothelial cells; endo cells—human adult microvascular endothelial cells; cor—human cornea epithelial cells. Cells from different donors are indicated by d1, d2 etc. The columns indicate the genes that were used for the infections. The genomic DNA was isolated after permanent cell lines were established (at least 30 population doublings after infection). PCR analysis was employed to determine the genes that are integrated in the immortalised cell lines. To generate a digital map of the immortalisation detected genes were labelled with "1" and genes that were absent are designated with "0". Grey boxes represent those genes that were not used in the respective infection.

FIG. 4: Establishment of specialized endothelial cell lines. Depicted are the infections that led to immortalisation of HUVEC cells. The columns indicate the genes that were used for infections. Genomic DNA was isolated after permanent cell lines were established (at least 30 population doublings after infection). PCR analysis was employed to determine the genes that are integrated in the immortalised cell lines. The genes that were detected by PCR are designated with "1" whereas the genes that are absent are designated with "0". Grey boxes represent those genes that were not used in the respective infection. In the first round of infection all genes or a random mixture of at least 10 different genes were employed. In addition to the PCR determination of the immortalising genes the cell lines were also analysed for the expression of endothelial specific markers. The most suitable cell lines (and gene combinations) were used in following infection rounds to narrow the set of genes responsible for immortalising HUVECs. In addition to narrowing the set of genes the established cell lines were characterized for the expression of endothelial specific markers. In round three all combinations resulted in the immortalisation of HUVECs and gave rise to cell lines with the desired phenotype. As an example, the infection employing Myc, Id1, Fos is shown in the FIGS. 6, 7 and 8.

Figure 1:
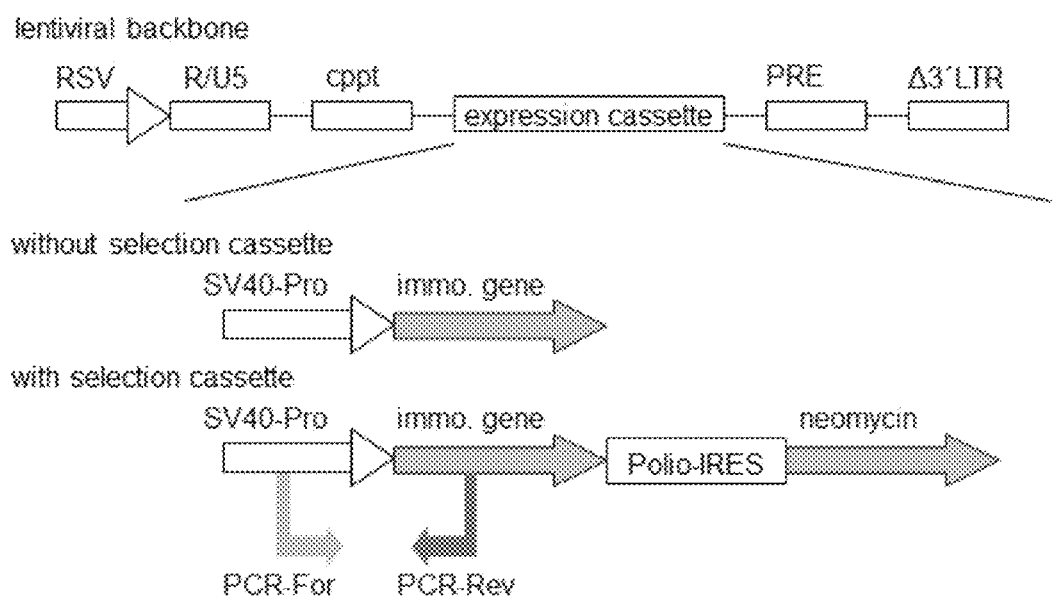
FIG. 1: Setup of immortalising lentiviral vectors transducing immortalisation cassette. A third generation lentiviral vector was used as backbone for the gene expression cassettes. All lentiviral vectors are self-inactivating with a deletion in the 3'LTR which destroys 5' promoter activity upon infection. The expression cassette coding for the immortalising gene comprise a SV40 promoter and the immortalising gene alone (without selection cassette) or in combination with the selection marker neomycin (with selection cassette). In case of the latter the transcription of neomycin was initiated through an internal ribosomal entry site (Polio-IRES). 3' to the expression cassette a Hepatitis B Virus posttranscriptional regulatory element (PRE) is placed. The genes present in the established cell lines were determined by PCR. For this purpose, a primer binding within the SV40 promoter was used as a forward primer and a primer specifically recognizing the respective immortalising gene was used as a reverse primer. The following genes were transduced without a selection cassette: PymT; HoxA9; Bmi1; Id3; Myb; core; Klf4; Oct3/4; Rex1; Bcl2. The following genes were transduced with a selection cassette: Myc; β-cat; Id1; TAg; Fos; E2f1; Jun; Ns1; Sox2; Id2; Lmo2; Nanog; Nfe2l2; Yap1; E7; E6; Gli1; Suz12; Ezh2; Zfp217; RhoA; v-Myc; Id4. PRE: Hepatitis B Virus posttranscriptional regulatory element; cppt: central polypurine tract; immo. gene: one of the abovementioned expansion genes; RSV: Rous sarcoma virus promoter; PCR-For: forward primer; PCR-Rev: reverse primer; Polio-IRES: internal ribosomal entry site of the poliovirus; SV40-Pro: SV40 promoter.

shows a heterogenous eGFP signal which demonstrates that this cell line is derived from hepatocytes and another cell type.

EXAMPLES

The following examples are for illustrative purposes only and do not limit the invention described above in any way.

Example 1

Identification of Immortalising Genes

The aim of the technology of the invention is to provide biologically relevant mammalian cells in unlimited numbers. To solve the limitations of the current process of cell line establishment, we identified 33 different genes that could induce immortalisation of mammalian cells. Included in this set of genes are viral oncogenes, mammalian oncogenes, genes that are overexpressed in tumor cells and genes that inhibit differentiation. The immortalising genes that were employed are listed in table 1 in which the abbreviations are given that are used in this description. In addition the official gene title, geneID and the gene symbol are provided which are taken from the NCBI database as well as the species/organism from which the gene was derived from. The employed cellular genes were either from human or from mouse. However, for the present invention also homologues from other species can be used.

TABLE 1

Overview of the employed genes

| Abbreviation | gene title | gene symbol | GeneID | species |
|---|---|---|---|---|
| Id2 | inhibitor of DNA binding 2 (Id2) | ID2 | 3398 | human |
| Fos | v-fos FBJ murine osteosarcoma viral oncogene homolog | FOS | 2353 | human |
| NS1 | NS1 nonstructural protein NS1 | NS1 | 956533 | Influenza Virus |
| Jun | jun oncogene | JUN | 3725 | human |
| E2F1 | *Homo sapiens* E2F transcription factor 1 (E2F1) | E2F1 | 1869 | human |
| βCat | CTNNB1 catenin (cadherin-associated protein), beta 1, 88 kDa | CTNNB1 | 1499 | human |
| TAg | SV40gp6 large T antigen | SV40gp6 | 1489531 | Simian Virus 40 |
| Myb | v-myb myeloblastosis viral oncogene homolog (avian) | MYB | 4602 | human |
| Id3 | inhibitor of DNA binding 3, dominant negative helix-loop-helix protein | ID3 | 3399 | human |
| E7 | E7 transforming protein | E7 | 1489079 | Human papillomavirus type 16 |
| E6 | E6 transforming protein | E6 | 1489078 | Human papillomavirus type 16 |
| Bcl2 | B-cell leukemia/lymphoma 2 | Bcl2 | 12043 | murine |
| HoxA9 | homeobox A9 | HOXA9 | 3205 | human |
| Bmi1 | Bmi1 polycomb ring finger oncogene | Bmi1 | 12151 | murine |
| PymT | MPyVgp2 middle t-antigen | MPyVgp2 | 1489533 | Polyoma Virus |
| Core | core protein | | * | Hepatitis C Virus |
| Oct3 | POU class 5 homeobox 1 | POU5F1 | 5460 | human |
| Klf4 | Kruppel-like factor 4 | KLF4 | 9314 | human |
| Id1 | inhibitor of DNA binding 1, dominant negative helix-loop-helix protein | ID1 | 3397 | human |
| Myc | v-myc myelocytomatosis viral oncogene homolog (avian) | MYC | 4609 | human |
| Lmo2 | LIM domain only 2 (Lmo2), | Lmo2 | 4005 | murine |
| Nfe2L2 | nuclear factor (erythroid-derived 2)-like 2 | NFE2L2 | 4780 | human |
| Yap1 | yes-associated protein 1 | Yap1 | 22601 | murine |
| Nanog | Nanog homeobox (Nanog) | Nanog | 71950 | murine |
| Sox2 | SRY (sex determining region Y)-box 2 | SOX2 | 6657 | human |
| RhoA | ras homolog gene family, member A | RHOA | 387 | human |
| Ezh2 | enhancer of zeste homolog 2 (*Drosophila*) | EZH2 | 2146 | human |
| Gli1 | glioma-associated oncogene homolog 1 (zinc finger protein) | GLI1 | 2735 | human |
| v-Myc | v-myc myelocytomatosis viral related oncogene, neuroblastoma derived (avian) | MYCN | 4613 | human |
| Suz12 | suppressor of zeste 12 homolog | SUZ12 | 23512 | human |
| ZFP217 | zinc finger protein 217 | ZNF217 | 7764 | human |
| Id4 | inhibitor of DNA binding 4, dominant negative helix-loop-helix protein | ID4 | 3400 | human |
| Rex | *Mus musculus* zinc finger protein 42 (Zfp42) | Zfp42 | 22702 | murine |

* For the core protein of the Hepatits C Virus no GeneId exists. The HCV core protein is cleaved from an mRNA comprised of multiple genes and the gene employed corresponds to the NCBI reference sequence NP_751919.1.

Example 2

Recombinant Expression of the Immortalising Genes in Primary Cells

To achieve immortalisation of primary cells, the immortalising genes have to be recombinantly expressed in primary mammalian cells. For this purpose any gene or protein transduction method can be employed that allows recombinant expression of the immortalising genes. Furthermore, any gene expression cassette (whether integrated in the host cell genome or not) that is capable of inducing the expression of the immortalising genes can be employed.

In the following examples lentiviral particles were used to transduce primary cells and the SV40 promoter was used to drive the expression of the immortalising genes. The lentiviral vectors that were used are third generation self-inactivating lentiviral vectors. In these lentiviral plasmids the viral sequences have been successively reduced. In this vector generation not only the accessory genes vpr, nev, rev and gag/pol are deleted but also the viral LTRs are modified so that the viral promoter/enhancer sequence is deleted. Furthermore, in the 5'LTR a RSV promoter is included instead of the wtHIV promoter. In order to increase the titre, additional elements (1) the central polypurine tract (cppt) and (2) the posttranslational regulatory element from the Hepatitis B virus (PRE) were included in the lentiviral vector. These elements were arranged 5' (cppt) and 3' (PRE) to the expression cassette.

The expression cassette comprised a SV40 promoter and the immortalising gene(s) alone (without selection cassette) or in combination with the selection marker neomycin (with selection cassette). In case of the latter the transcription of neomycin was initiated by an internal ribosomal entry site (Polio-IRES). 3' to the expression cassette a Hepatitis B Virus posttranscriptional regulatory element (PRE) is placed. A schematic drawing of the different vector setups used is shown in FIG. 1.

The following genes were transduced without a selection cassette:
PymT; HoxA9; Bmi1; Id3; Myb; core; Klf4; Oct3/4; Rex1; Bcl2

The following genes were transduced with a selection cassette:
Myc; β-cat; Id1; TAg; Fos; E2f1; Jun; Ns1; Sox2; Id2; Lmo2; Nanog; Nfe212; Yap1; E7; E6; Gli1; Suz12; Ezh2; Zfp217; RhoA; v-Myc; Id4

The expression cassette encoding the hepatocyte specific albumin promoter was also integrated into a self inactivating lentivirus backbone. The expression cassette is comprised of the murine albumin enhancer and promoter region followed by the reporter gene enhanced green fluorescent protein and the posttranslational regulatory element from the Woodchuck Hepatitis Virus (WPRE).

For the production of the viral particles a transient transfection protocol was used which is based on calcium phosphate precipitation of four different plasmids. The production of the lentiviral particles was performed in HEK293T cells with lentiviral helper plasmids from the ViraPower™ Lentiviral Expression System (Invitrogen). A day before transfection, HEK293T cells were plated at a cell density of ~20000 cells per cm$^2$. For the calcium phosphate precipitation the four plasmids encoding the helper functions gag/pol (pLP1), rev (pLP2) and the VSVg (pVSVg) surface protein along with one of the transfer plasmids (see the abovementioned list of expression constructs) were mixed. For a transfection of a culture dish with an area of 140 cm$^2$ the following amounts of the different plasmids were used: 14 μg pLP1 (gag/pol), 4.6 μg pLP2 (rev); 7.8 μg pLP/VSVg (VSVg), 20 μg transfer plasmid (expression construct harbouring the immortalisation gene or the albumin reporter construct).

The different plasmids were resuspended in 500 μl of 250 mM CaCl$_2$ solution and then this mixture was dropwise added to 500 μl of HEBS solution under continuous vortexing and then kept for 10 minutes at room temperature for precipitation. This suspension was added to the culture medium of the HEK293T cells. The following day the media was aspirated and 15 ml fresh media was added. 24 h later the supernatant containing the lentiviral particles was collected. For a second production again 15 ml fresh media was added to the producer cells and after 24 h the supernatant containing the lentiviral particles was collected. The lentivirus containing supernatant was filtrated with a 0.45 μm filter to remove cell debris and stored at −70° C. until use.

The titre of the respective lentiviruses was evaluated using NiH3T3 cells. The titration was performed on 12 well plates. For this purpose 50.000 cells were plated a day before infection. On the day of infection the media was aspirated and the virus containing supernatant was added to the cells for 12 h. The total volume of the infection was 400 μl and four different concentrations of the virus containing supernatant were used (1 μl; 4 μl; 40 μl; 400 μl). In addition, Polybrene was added to the infection with a final concentration of 8 μg/ml. Dependent on the expression construct the infected NiH3T3 cells were either titrated for G418 (with selection cassette) resistance or for transduction/integration by PCR (without selection cassette).

The titration for G418 resistance was started two days after infection with media containing 1 mg/ml G418. After two weeks of selection the confluency of the cells was scored. In further experiments only those virus stocks were used that gave rise to confluent plates in the dilutions 400 μl; 40 μl and 4 μl of the HEK293 cell culture supernatant. The titration for transduction/integration of the expression constructs without the selection cassette was performed by PCR of the genomic DNA of the infected NiH3T3 cells. For this purpose, the genomic DNA of the infected NiH3T3 cells was isolated two days after infection and assayed by PCR for the integration of the immortalising gene. The details of the DNA isolation and the PCR are given below. In further experiments only those viral stocks were used that showed integration of the immortalising gene in the 1 μl dilution of the HEK293 cell culture supernatant.

For the establishment of the mammalian cell systems, lentiviruses harbouring the different immortalising genes were mixed. For this purpose, viral stocks with a sufficient titre were premixed. These master mixes were stored in 1 ml aliquots at −70° C. until use. The following master mixes were prepared and used for infection if not indicated otherwise:

All—all immortalising genes (as listed in table 1) were included;
MBG—all immortalising genes (as listed in table 1) with the exception of TAg, E6, E7 and Myc;
1-10—Id2, Fos, NS1, Jun, E2F1, βCat, Myb, Id3, Bcl2, HoxA9;
11-20—Bmi1, PymT, Core, Oct3, Klf4, Id1, Lmo2, Nfe2L2, Yap1, Nanog;
21-29—Sox2, RhoA, Ezh2, Gli1, v-Myc, Suz12, ZFP217, Id4, Rex.

Example 3

Establishment of Mammalian Cell Systems

The described technology allows the establishment of novel mammalian cell lines independent of the species, cell type, genotype of the donor, or the age of the donor. For this purpose the primary cells of interest can be transduced with the whole set of 33 immortalising genes or with a suitable smaller subset of immortalising genes. In the following examples the utility of this technology was proven with the establishment of novel mammalian cell lines derived from different species (murine, bovine, human), from different cell types (fibroblasts, bone marrow stroma cells, macrophages, endothelial cells, osteoblasts, chondrocytes, keratinocytes, lung epithelial cells, cornea epithelial cells, hepatocytes), from different genotypes (fibroblasts, bone marrow stroma cells) and from young (human umbilical cord endothelial cells and keratinocytes) and adult (human adult keratinocytes, human adult microvascular endothelial cells) individuals. However, the invented technology is not restricted to the mentioned examples but can be applied to any cell type and to cells of any mammalian species. Also, different genes which have a function equivalent to those tested may be used.

All primary cells or cell lines were maintained at 37° C. in a humidified atmosphere with 5% $CO_2$. The following primary cell types were used for the immortalisation procedure: primary human foreskin fibroblasts FS4 (Gupta et al., Proc Natl Acad Sci U.S.A. 1979 October; 76(10):4817-21.) and hDP (isolation detailed in Mujaj S et al., Tissue Eng Part A. 2010 April; 16(4):1407-20.); human adult dermal fibroblasts (Promocell GmbH); mouse adult ear fibroblasts transgenic with an MxLuc2 bac (Pulverer et al., J Virol. 2010 September; 84(17):8626-38; isolation detailed in May et al., 2005 Oct. 17; 120(1):99-110); human umbilical vein endothelial cells (HUVEC—from ProVitro GmbH), human dermal microvascular endothelial cells (HMVEC—from ProVitro GmbH); human epidermal adult keratinocytes (from ProVitro GmbH) and human keratinocytes from the foreskin (isolation described in Aasen and Belmonte, Nat Protoc. 2010; 5(2):371-82.); bovine macrophages (isolation described in Werling et al., Immunology. 2004 January; 111(1):41-52.) adult human osteoblasts (isolation detailed in Hernandez et al., Arthritis Rheum. 2008 June; 58(6):1696-700); adult human chondrocytes (isolation detailed in Fay et al., Arthritis Res Ther. 2006; 8(6):R189); adult human lung epithelial cells (isolation detailed in Elbert et al., 1999, Pharm Res. 1999 May; 16(5):601-8.), adult human bone marrow stroma cells (isolation detailed in Zhang et al., Ann Hematol. 1999 July; 78(7):305-14.), cornea epithelial cells (from Cell Systems GmbH), adult murine hepatocytes (isolation detailed in Haridass et al. Am J Pathol. 2009 October; 175(4): 1483-92).

Fibroblasts, bone marrow stroma cells, bovine macrophages and osteoblasts were cultivated in IMDM supplemented with 10% fetal calf serum, 2 mM glutamine, 0.1 mM non essential amino acids, 0.1 mM β-mercaptoethanol and 100 U penicillin, 100 µg/ml streptomycin. Hepatocytes were cultivated in DMEM basal media supplemented with 10% fetal calf serum, 2 mM glutamine, 100 U penicillin and 100 µg/ml streptomycin. Chondrocytes and cornea epithelial cells were cultivated in a 1 to 1 mixture of HamF12 and DMEM basal media. This mixture was supplemented with 10% fetal calf serum, 2 mM glutamine, 0.1 mM non essential amino acids, 0.1 mM β-mercaptoethanol and 100 U penicillin, 100 µg/ml streptomycin. Adult lung epithelial cells were cultivated in SABM Basal Medium supplemented with SAGM SingleQuot Kit (Lonza). The keratinocytes were cultivated in DermaLife K Cell Culture Medium Kit which is comprises the DermaLife™ basal medium and supplements (LifeFactors K, CellSystems GmbH). HUVECs were cultivated in endothelial-cell basal medium EBM (Lonza) supplemented with EGM-MV single quots (Lonza). HMVECs were cultivated in endothelial-cell basal medium EBM-2 (Lonza) supplemented with EGM-2 MV singlequots (Lonza). Endothelial cells were cultivated in gelatine-coated tissue-culture flasks. For this purpose cell culture plates were covered with a 0.1% (HUVECs) or 1% (HMVECs) gelatine solution for 30 minutes at 37° C. The gelatine was aspirated and the endothelial cells were plated. Keratinocytes were cultivated either in normal tissue-culture flasks or flasks that were coated with collagen I.

For immortalisation, primary cells were seeded on 6-well plates and infected with the combinations of respective viruses (master mixes or defined infections). The cells were plated to reach a confluency of 80% on the day of infection. For infection, the cultivation media was aspirated and 1 ml of the lentiviral master mixes as well as 200 µl of the respective cultivation media was added to the cells. In case of infections with fewer than 10 immortalising genes, 100 µl of each lentiviral stock was used and the infection volume was set to 1 ml with the respective cultivation media. In case of the hepatocytes the infection mixture consisted of 500 µl of the lentiviral immortalizing master mixes and 500 µl of the albumin eGFP reporter lentivirus as well as 200 µl of the cultivation media. All infections were supplemented with Polybrene in a final concentration of 8 µg/ml. The primary cells were infected for 8-12 h at 37° C. in a humidified atmosphere. In all cases a non-infected control was included to determine the time point at which the primary cells enter crisis.

Figure 2:
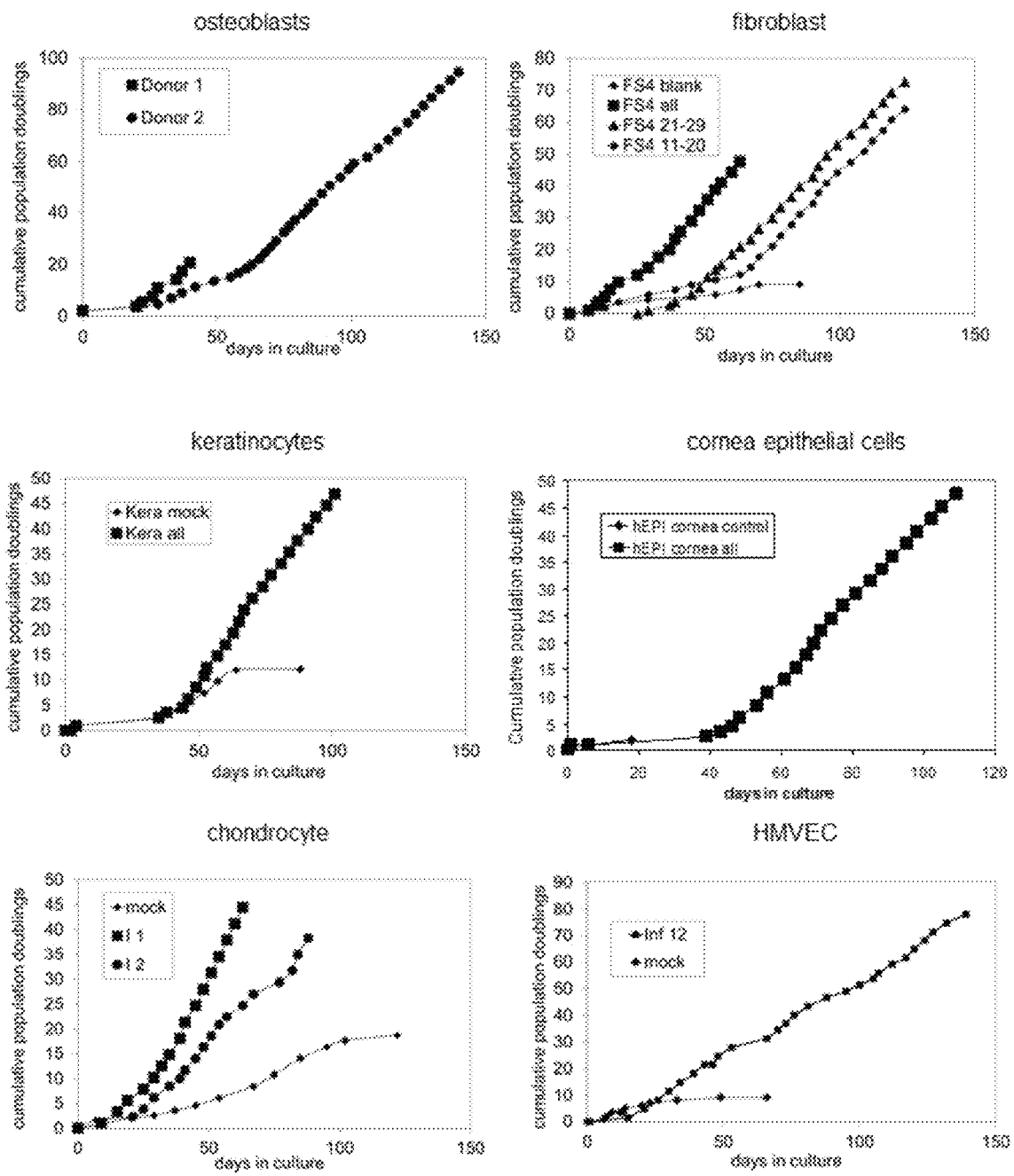
FIG. 2: Immortalisation of different cell types. The indicated human primary cells were infected and expanded. Shown are representative examples of the cumulative population doublings of the established cell lines. In all cases a mock infection was used as a control. In case of the cornea epithelial cells and the osteoblasts, these cells ceased their division 14 days after infection and are therefore not included in the graph.

For the establishment of cell lines, two strategies were used: either the infected cells were selected with 0.4 mg/ml G418, or they were selected for their growth advantage due to the expression of the immortalising gene. For FS4 cells both strategies were compared and gave rise to similar results with respect to the proliferation pattern of the established cell lines and with respect to the pattern of the integrated immortalising genes. Therefore, the selection strategy was applied if the primary cells were judged as robustly proliferating (e.g. fibroblasts, endothelial cells) whereas no selection pressure was applied if the primary cells were not or only marginally proliferating (e.g. cornea epithelial cells, adult dermal keratinocytes). For the establishment of the cell lines the colonies were pooled and further expanded independent of G418 resistance or proliferation advantage. For the establishment of the cell lines the cells were passaged when they reached confluency. In the beginning of the immortalisation process the cells were splitted with a ratio of 1 to 3. After the cells adapted a robust proliferation behaviour (meaning that they reached confluency within three days after plating) the splitting ratio was adjusted to 1 to 5 or 1 to 10 depending on the cell type. The results of the immortalisation of different human primary cells are shown in FIG. 2. The indicated human primary cells were infected and expanded. Shown are the cumulative population doublings for some established cell lines.

Example 4

Identifying the Genes Responsible for Immortalisation

The next step was the identification of the genes that were responsible for the immortalisation of the primary cells. For this purpose a PCR strategy was developed detecting the genes present in the genome of the immortalised cell lines. Because of the selective advantage that the immortalisation genes or better the combinations of genes are conferring to the infected cells a long expansion period was chosen before the genomic DNA was isolated (>30 cumulative population doublings). This should ensure that the detected genes are indeed responsible for the immortalisation.

The genomic DNA was isolated with the following procedure. The cells were washed twice with PBS, and 500 µl (6 well) of lysis buffer (10 mM Tris, pH 7.5, 10 mM EDTA, 10 mM NaCl, 0.5% sodium dodecyl sulfate, and 1 mg/ml proteinase K (added fresh)) was added per well. The lysed cells were transferred to a 1.5 ml plastic tube and incubated overnight at 60° C. The next day, 75 mM sodium acetate (in ethanol) was added (1 ml). The tube was incubated at room temperature for 2h and then slowly turned up and down in order to visualize the genomic DNA pellet. Then the DNA solution was centrifuged in a table top centrifuge for 5 minutes at 5000 rpm. Afterwards the supernatant was discarded and the pellet was washed with 70% ethanol twice. After the final wash, the pellet was allowed to dry and dissolved in 30-50 µl TE (10 mM Tris, pH 7.5, 10 mM EDTA) or alternatively in $H_2O$ and stored at 4° C.

A schematic overview of the PCR strategy detecting the immortalising genes is shown in FIG. 1. Both primers bind in the expression cassette that is transduced by the lentiviral cassette. The 5' primer is located in the SV40 promoter whereas the 3' primer is specific for the respective immortalising gene (table 2).

TABLE 2

List of primers used for the detection of the immortalizing genes

| | Gene | Sequence | expected band primer |
|---|---|---|---|
| | | 5' Forward Primer | |
| | SV40for1 | Ggaggcctaggcttttgcaa (SEQ ID NO: 1) | |
| | | 3' Reverse Primer | |
| 1 | Id2 | GCAGGCTGACAATAGTGGGA (SEQ ID NO: 2) | 462 bp |
| 2 | Fos | GGATGATGCTGGGAACAGGA (SEQ ID NO: 3) | 1054 bp |
| 3 | NS1 | ATGTCCTGGAAGAGAAGGCA (SEQ ID NO: 4) | 678 bp |
| 4 | Jun | TTCCTCATGCGCTTCCTCTC (SEQ ID NO: 5) | 912 bp |
| 5 | E2F1 | CAGGGTCTGCAATGCTACGA (SEQ ID NO: 6) | 944 bp |
| 6 | βCat | TTATGCAAGGTCCCAGCGGT (SEQ ID NO: 7) | 806 bp |
| 7 | TAg | CACCTGGCAAACTTTCCTCA (SEQ ID NO: 8) | 1214 bp |
| 8 | Myb | CTTCTGGAAGCTTGTGGCCA (SEQ ID NO: 9) | 780 bp |
| 9 | Id3 | ATGACAAGTTCCGGAGCGAG (SEQ ID NO: 10) | 453 bp |
| 10 | E7 | GCCCATTAACAGGTCTTCCA (SEQ ID NO: 11) | 404 bp |
| 11 | E6 | ATTCGCCCTTTTACAGCTGG (SEQ ID NO: 12) | 636 bp |
| 12 | Bcl2 | TCTGCGAAGTCACGACGGTA (SEQ ID NO: 13) | 440 bp |
| 13 | HoxA9 | GTTTAATGCCATAAGGCCGG (SEQ ID NO: 14) | 515 bp |
| 14 | Bmi1 | GGGCCATTTCTTCTCCAGGT (SEQ ID NO: 15) | 782 bp |
| 15 | PymT | CATCTCGGGTTGGTGTTCCA (SEQ ID NO: 16) | 606 bp |
| 16 | Core | ACTTTACCCACGTTGCGCGA (SEQ ID NO: 17) | 487 bp |
| 17 | Oct3 | Gcaaagcagaaaccctcgtg (SEQ ID NO: 18) | 846 bp |
| 18 | Klf4 | Aagatcaagcaggaggcggt (SEQ ID NO: 19) | 1084 bp |
| 19 | Id1 | AGAAGCACCAAACGTGACCA (SEQ ID NO: 20) | 980 bp |
| 20 | Myc | AGTGGGCTGTGAGGAGGTTT (SEQ ID NO: 21) | 1001 bp |
| 21 | Lmo2 | TTTCCGTCCCAGCTTGTAGT (SEQ ID NO: 22) | 822 bp |
| 22 | Nfe2L2 | GCTGCTGAAGGAATCCTCAA (SEQ ID NO: 23) | 1008 bp |
| 23 | Yap1 | GCCAGGATGTGGTCTTGTTC (SEQ ID NO: 24) | 950 bp |
| 24 | Nanog | TATGGAGCGGAGCAGCATTC (SEQ ID NO: 25) | 935 bp |
| 25 | Sox2 | Ctcgcagacctacatgaacg (SEQ ID NO: 26) | 846 bp |

TABLE 2-continued

List of primers used for the detection of the immortalizing genes

| | Gene | Sequence | expected band primer |
|---|---|---|---|
| 26 | RhoA | Aagcatttctgtcccaacgt (SEQ ID NO: 27) | 562 bp |
| 27 | Ezh2 | Acttcgagctcctctgaagc (SEQ ID NO: 28) | 1481 bp |
| 28 | Gli1 | Caccacatcaacagcgagca (SEQ ID NO: 29) | 1144 bp |
| 29 | v-Myc | Gacaccctgagcgattcaga (SEQ ID NO: 30) | 1052 bp |
| 30 | Suz12 | Taccctggaagtcctgcttg (SEQ ID NO: 31) | 769 bp |
| 31 | ZFP217 | Caagaagggagcaccgacaa (SEQ ID NO: 32) | 1188 bp |
| 32 | Id4 | Cagcaaagtggagatcctgc (SEQ ID NO: 33) | 652 bp |
| 33 | Rex | Gcgagctcattacttgcagg (SEQ ID NO: 34) | 920 bp |

The PCR was performed using the Mango-Taq Polymerase Kit (Bioline). The annealing temperature was 58° C. with an elongation time of 30 sec. PCR followed by an denaturation step at 94° C. for 1 min which was repeated in 30 cycles. As template, 0.1 µg genomic DNA of the infected cells was used. Each gene was analysed with a separate PCR. The PCRs were analysed on a 1 agarose gel and the genes were scored either as absent or present.

Figure 3:
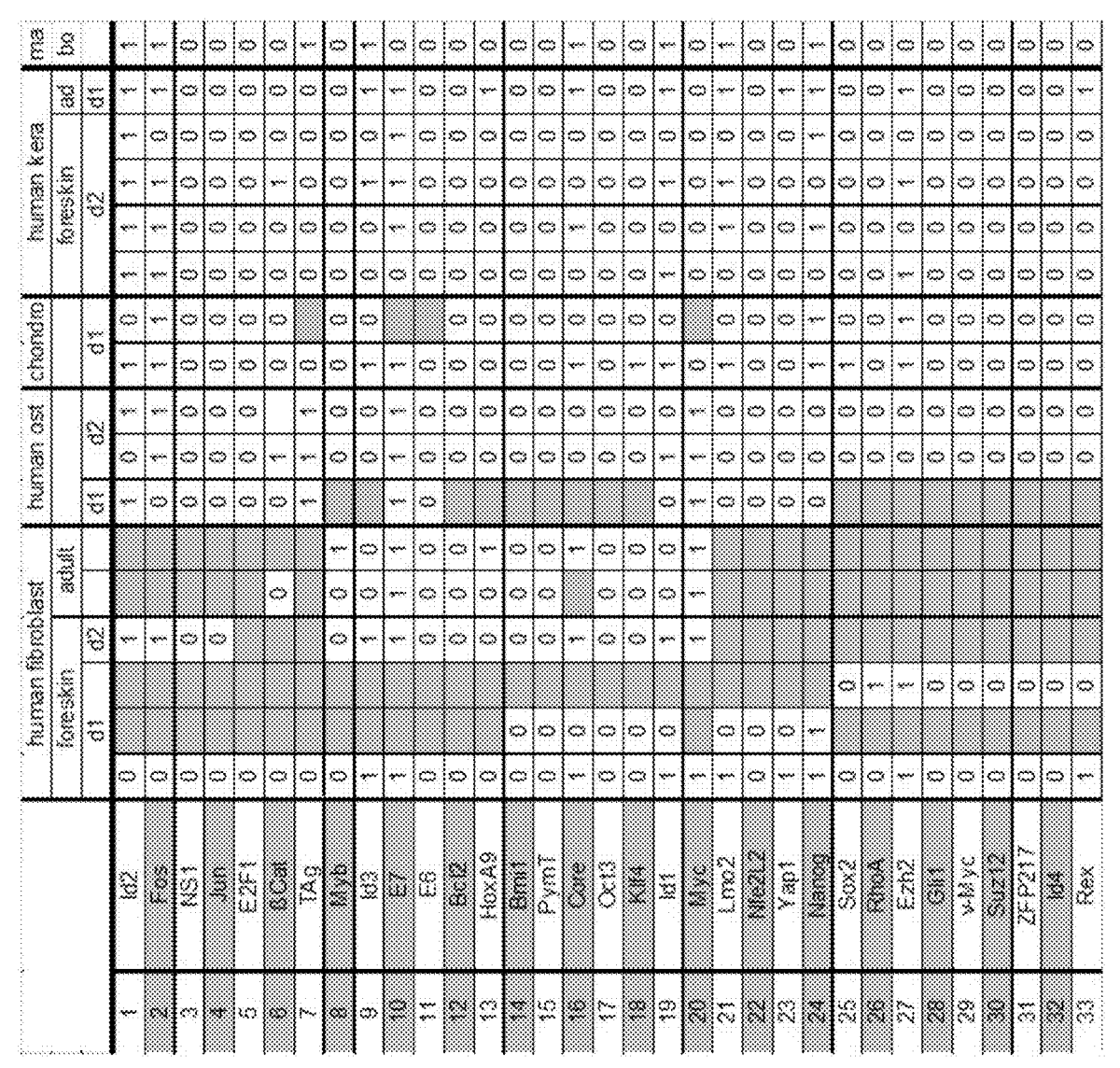
Figure 3:
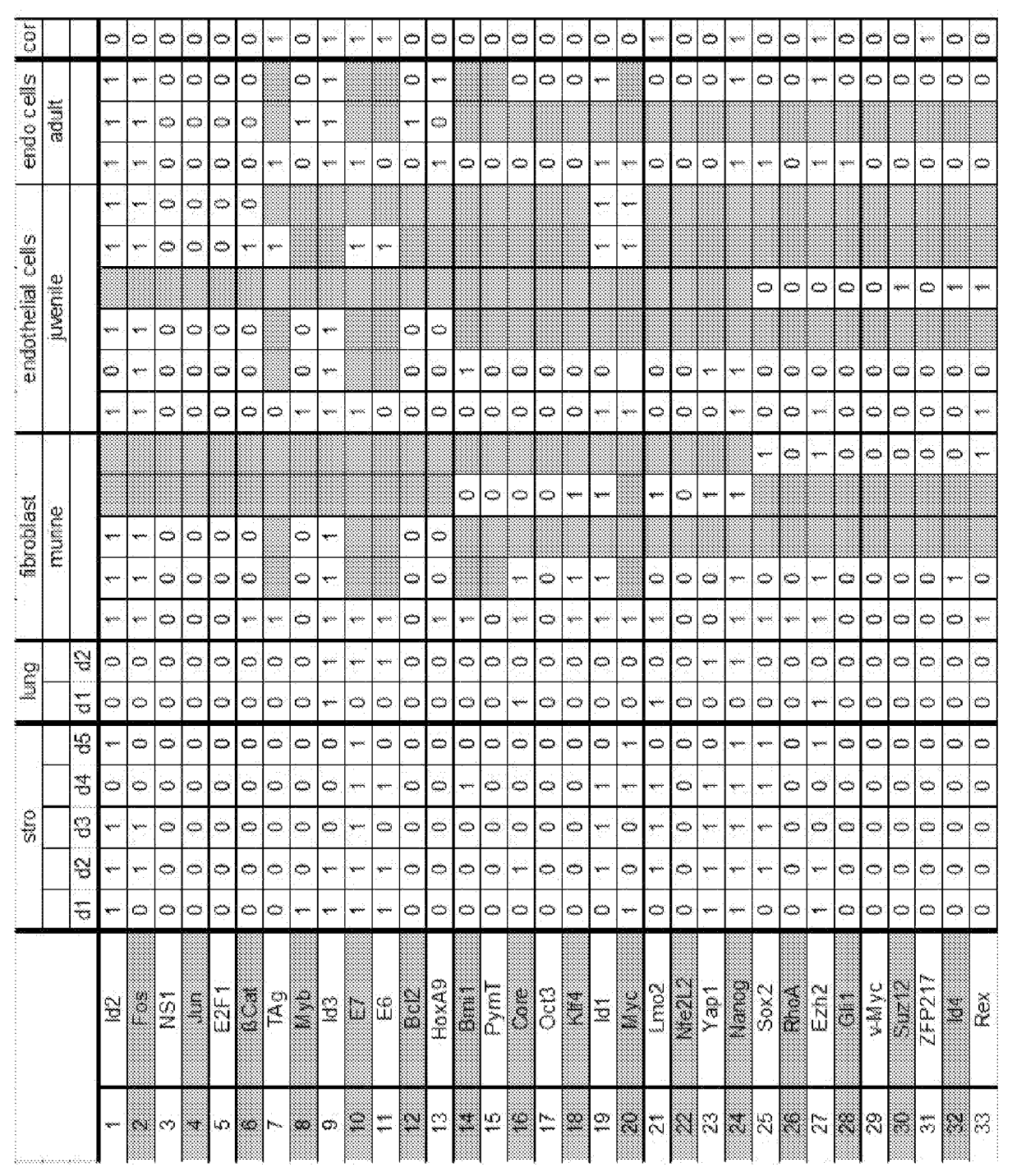

The results of these analyses were compiled into a heat map (FIG. 3). In this heat map of immortalisation the infections are depicted that led to immortalisation of the indicated cell types. The columns indicate the genes that were used for the infections. The genomic DNA was isolated after permanent cell lines were established (at least 30 population doublings after infection). PCR analysis was employed to determine the genes that are integrated in the immortalised cell lines. To generate a digital map of the immortalisation detected genes were labelled with "1" and genes that were absent are designated with "0". Grey boxes represent those genes that were not used in the respective infection.

For this analysis different cell types, cells from various species, cells from different donors and juvenile and adult cells were employed (FIG. 3). Fibroblast cell lines were established from murine and from human origin. For the human cells, foreskin (juvenile) and dermal fibroblasts (adult) were used. In addition, foreskin fibroblasts from two different donors (d1 and d2) were used. Human endothelial cell lines were established from human umbilical vein endothelial cells (endothelial cells—juvenile) and from human microvascular endothelial cells (endo cells—adult). In addition, human cornea epithelial cells (cor), human keratinocytes adult (ad) and juvenile (from foreskin) (human kera), human bone marrow stroma cells from five different donors (stro), human lung epithelial cells (lung), bovine macrophages (ma), human osteoblasts (human ost) and human chondrocytes (chondro) were established.

From the results of the heat map the frequency of the respective genes was calculated. This was done to rank the different immortalising genes. For this purpose the number of infections in which a gene was used was divided by the number of detections. This ranking was performed for all cell types and also separately only for infections of fibroblasts. Highlighted with stripes are those genes that showed a frequency of 0.5 or greater (table 3).

TABLE 3

Frequency of genes in the established cell lines

| | | all cell types | | | fibroblasts | | | hepatocytes | | |
|---|---|---|---|---|---|---|---|---|---|---|
| | | inf.[1] | det.[2] | fre.[3] | inf. | det. | fre. | inf. | det. | fre. |
| 1 | Id2 | 18 | 14 | 0.78 | 5 | 4 | 0.80 | 8 | 0 | 0 |
| 2 | Fos | 18 | 15 | 0.83 | 5 | 4 | 0.80 | 8 | 3 | 0.375 |
| 3 | NS1 | 18 | 0 | 0.00 | 5 | 0 | 0.00 | 1 | 0 | 0 |
| 4 | Jun | 18 | 0 | 0.00 | 5 | 0 | 0.00 | 1 | 0 | 0 |
| 5 | E2F1 | 17 | 0 | 0.00 | 4 | 0 | 0.00 | 1 | 0 | 0 |
| 6 | βCat | 18 | 2 | 0.11 | 5 | 1 | 0.20 | 8 | 0 | 0 |
| 7 | TAg | 9 | 5 | 0.56 | 2 | 1 | 0.50 | 8 | 3 | 0.375 |
| 8 | Myb | 17 | 3 | 0.18 | 7 | 1 | 0.14 | 8 | 0 | 0 |
| 9 | Id3 | 18 | 14 | 0.78 | 7 | 5 | 0.71 | 8 | 1 | 0.125 |
| 10 | E7 | 12 | 12 | 1.00 | 5 | 5 | 1.00 | 8 | 3 | 0.375 |
| 11 | E6 | 12 | 3 | 0.25 | 5 | 1 | 0.20 | 8 | 0 | 0 |
| 12 | Bcl2 | 17 | 1 | 0.06 | 7 | 0 | 0.00 | 8 | 0 | 0 |
| 13 | HoxA9 | 17 | 5 | 0.29 | 7 | 2 | 0.29 | 8 | 0 | 0 |
| 14 | Bmi1 | 14 | 2 | 0.14 | 7 | 1 | 0.14 | 8 | 0 | 0 |
| 15 | PymT | 14 | 0 | 0.00 | 7 | 0 | 0.00 | 1 | 0 | 0 |
| 16 | Core | 15 | 7 | 0.47 | 7 | 5 | 0.71 | 8 | 2 | 0.25 |
| 17 | Oct3 | 16 | 0 | 0.00 | 8 | 0 | 0.00 | 1 | 0 | 0 |
| 18 | Klf4 | 16 | 4 | 0.25 | 8 | 3 | 0.38 | 8 | 7 | 0.875 |
| 19 | Id1 | 19 | 12 | 0.63 | 8 | 5 | 0.63 | 8 | 0 | 0 |
| 20 | Myc | 13 | 10 | 0.77 | 5 | 5 | 1.00 | 8 | 1 | 0.125 |
| 21 | Lmo2 | 14 | 6 | 0.43 | 5 | 3 | 0.60 | 8 | 1 | 0.125 |
| 22 | Nfe2L2 | 14 | 0 | 0.00 | 5 | 0 | 0.00 | 1 | 0 | 0 |

TABLE 3-continued

Frequency of genes in the established cell lines

| 23 | Yap1 | 14 | 4 | 0.29 | 5 | 2 | 0.40 | 8 | 0 | 0 |
| 24 | Nanog | 14 | 13 | 0.93 | 5 | 5 | 1.00 | 8 | 0 | 0 |
| 25 | Sox2 | 14 | 4 | 0.29 | 5 | 2 | 0.40 | 8 | 0 | 0 |
| 26 | RhoA | 14 | 2 | 0.14 | 5 | 2 | 0.40 | 8 | 0 | 0 |
| 27 | Ezh2 | 14 | 12 | 0.86 | 5 | 5 | 1.00 | 8 | 0 | 0 |
| 28 | Gli1 | 14 | 1 | 0.07 | 5 | 0 | 0.00 | 8 | 0 | 0 |
| 29 | v-Myc | 14 | 0 | 0.00 | 5 | 0 | 0.00 | 1 | 0 | 0 |
| 30 | Suz12 | 14 | 1 | 0.07 | 5 | 0 | 0.00 | 8 | 0 | 0 |
| 31 | ZFP217 | 14 | 1 | 0.07 | 5 | 0 | 0.00 | 8 | 0 | 0 |
| 32 | Id4 | 14 | 2 | 0.14 | 5 | 1 | 0.20 | 8 | 2 | 0.25 |
| 33 | Rex | 14 | 6 | 0.43 | 5 | 3 | 0.60 | 8 | 0 | 0 | inf.[1] = infection;
det.[2] = detected;
fre.[3] = frequency

The ranking identifies (i) the set of genes that are particularly suitable for establishing novel mammalian cell lines. These genes are: Id2; Fos, βcat; TAg, Myb; Id3; E7; E6; Bcl2; HoxA9; Bmi1; core; Klf4; Id1; Myc; Lmo2; Yap1; Nanog; Sox2; RhoA; Ezh2; Gli1; Suz12; ZFP217, Id4; Rex; of these, a) Id1, Id2, and Id3 are members of the Id gene family, b) Nanog, Sox2, and Klf4 are genes involved in maintaining pluripotency, and c) E7, Fos, Myc, Bcat, RhoA, Myb, Core, Lmo2, E6, Sv40 large T antigen, Yap1, Gli1, Suz12, Ezh2, Bmi1, and Rex are genes facilitating the progression of the cell cycle; it is reasonable to assume that these genes can be substituted with other genes of the same category (i.e. those not mentioned in these lists, like e.g. homologues from other species or other genes from the same gene family); (ii) a core set of immortalising genes which show a frequency of 0.5 or greater and are therefore involved in the immortalisation in more than 50% of the infections. Importantly, this core set of genes can vary depending on the cell-type. This becomes evident when the rankings of the fibroblast and hepatocyte immortalisation are compared with all immortalisations. The core set of genes is: Id2; Fos; TAg; Id3; E7; core; Id1; Myc; Lmo2; Nanog; Ezh2; Rex.

An important feature of this technology is its great efficiency. All cell lines that were established from the different primary cells were established by the first trial and with only one infection cycle. It is important to note that the time required for the generation of the respective cell lines depends on the cell type. From the data it can be concluded that more juvenile cells (e.g. HUVEC) or cells with a greater intrinsic proliferation capacity (e.g. osteoblasts, fibroblasts) reach 30 cumulative population doublings within 60 days whereas cells isolated from adult individuals (e.g. HMVEC) or from highly differentiated cells (e.g. cornea epithelial cells) require a longer time period (~80-90 days) to reach 30 cumulative population doublings (table 4).

TABLE 4

Time required for the generation of novel cell lines

| cell type | species | time in days required for 30 cumulative PDL | independent immortalisations |
| --- | --- | --- | --- |
| fibroblast | human | 59.1 | 7 |
| osteoblasts | human | 58.0 | 3 |
| chondrocytes | human | 66.5 | 2 |
| cornea epithelial cell | human | 85.0 | 1 |
| keratinocytes | human | 77.0 | 1 |
| umbilical cord endothelial cells | human | 58.1 | 11 |
| microvascular endothelial cells | human | 92.0 | 3 |
| fibroblast | murine | n.a.* | 5 |

*the murine adult ear fibroblasts were not expanded until cumulative PDL 30. They were judged immortal as the respective the mock infected control ceased the proliferation after 5 passages ~10 cumulative PDL and the infected MAEF showed robust proliferation until cumulative PDL 25

Another important aspect is that there is not only one single possible combination of genes to immortalise the respective cell lines but instead various different combinations were identified for the immortalisation of the primary cells. Some examples of these combinations are listed in table 5.

TABLE 5

Combination of genes conferring immortalization

| cell type | species | donor | genes |
| --- | --- | --- | --- |
| fibroblast (foreskin) | human | d1 | Id2, Fos, TAg, Id3, E7, Bcl2, Core, Id1, Myc, Lmo2, Yap1, Nanog, Sox2, Ezh2, Rex |
| fibroblast (foreskin) | human | d1 | Id3, E7, Core, Id1, Myc, Lmo2, Yap1, Nanog, Ezh2, Rex |
| fibroblast (foreskin) | human | d1 | core, Id1, Lmo2, Nanog |
| fibroblast (foreskin) | human | d1 | RhoA, Ezh2 |
| fibroblast (foreskin) | human | d2 | Id2, Fos, Id3, E7, core, Id1, Myc |
| fibroblast (adult) | human | d3 | E7, Myc |
| fibroblast (adult) | human | d3 | Myb, E7, HoxA9, Core, Myc |
| fibroblast (adult; ear) | murine | | Id2, Fos, βcat, TAg, Id3, E7, E6, HoxA9, Bmi1, core, Klf4, Id1, Myc, Lmo2, Nanog, Sox2, RhoA, Ezh2, Rex |
| fibroblast (adult; ear) | murine | | Id2, Fos, Id3, core, Klf4, Id1, Nanog, Ezh2, Id4 |
| fibroblast (adult; ear) | murine | | Id2, Fos, Id3 |
| fibroblast (adult; ear) | murine | | Klf4, Id1, Lmo2, Yap1, Nanog |
| fibroblast (adult; ear) | murine | | Sox2, Ezh2, Rex |
| endothelial cell (umbilical cord) | human | | Id2, Fos, Myb, Id3, E7, Id1, Myc, Nanog, Ezh2, Rex |
| endothelial cell (umbilical cord) | human | | Fos, Id3, Bmi1, Yap1, Nanog |
| endothelial cell (umbilical cord) | human | | Id2, Fos, Id3 |
| endothelial cell (umbilical cord) | human | | Suz12, Id4, Rex |
| endothelial cell (umbilical cord) | human | | Id2, Fos, βcat, TAg, E7, E6, Id1, Myc |
| endothelial cell (umbilical cord) | human | | Id2, Fos, Id1, Myc |
| endothelial cell (umbilical cord) | human | | Id2, Id1, Myc |
| endothelial cell (umbilical cord) | human | | Id2, Fos, Id1 |
| endothelial cell (umbilical cord) | human | | Fos, Id1, Myc |
| endothelial cell (umbilical cord) | human | | Id2, Fos, Myc |
| endothelial cell (adult microvascular) | human | | Id2, Fos, Myb, Id3, Bcl2, |

TABLE 5-continued

Combination of genes conferring immortalization

| cell type | species | | donor genes |
|---|---|---|---|
| endothelial cell (adult microvascular) | human | | Id2, Fos, Id3, HoxA9, Id1, Nanog, Ezh2 |
| endothelial cell (adult microvascular) | human | | Id1, Id3, Fos, Ezh2, Nanog |
| endothelial cell (adult microvascular) | human | | E7, HoxA9, Sox2, Ezh2 |
| endothelial cell (adult microvascular) | human | | Id1, Id3, Fos, TAg, E7, HoxA9, Nanog, Sox2, Ezh2 |
| cornea epithelial cell | human | | TAg, Id3, E7, E6, Lmo2, Nanog, Ezh2, ZFP217 |
| osteoblast | human | d1 | Id2, TAg, E7, Myc |
| osteoblast | human | d2 | Fos, βcat, TAg, E7, Id1, Myc |
| osteoblast | human | d2 | Id2, Fos, TAg, E7, Myc |
| chondrocytes | human | | Id2, Fos, Id3, E7, core, Klf4, Id1, Lmo2, Nanog, Sox2, Ezh2 |
| chondrocytes | human | | Fos, Nanog, Ezh2 |
| macrophages | bovine | | Id2, Fos, TAg, Id3, core, Id1, Lmo2, Nanog |
| keratinocyte (adult) | human | d1 | Id3, E7, Id1, Lmo2, Yap1, Nanog, Ezh2 |
| keratinocyte (foreskin) | human | d2 | Id2, Fos, Id1, Ezh2 |
| keratinocyte (foreskin) | human | d2 | Id2, Fos, E7, core, Lmo2, Nanog |
| keratinocyte (foreskin) | human | d2 | Id2, Fos, βcat, Id3, E7, Id1, Lmo2, Ezh2 |
| keratinocyte (foreskin) | human | d2 | Id2, E7, Nanog, Ezh2 |
| stroma cells (Bone marrow) | human | d1 | Id2, Myb, Id3, E7, E6, Myc, Yap1, Nanog, Ezh2 |
| stroma cells (Bone marrow) | human | d2 | Id2, Fos, Id3, E7, E6, core, Id1, Lmo2, Yap1, Nanog, Sox2, Ezh2 |
| stroma cells (Bone marrow) | human | d3 | Id2, Fos, E7, Id1, Lmo2, Yap1, Nanog, Sox2 |
| stroma cells (Bone marrow) | human | d4 | E7, E6, Bmi1, Id1, Myc, Lmo2, Yap1, Nanog, Sox2, |
| stroma cells (Bone marrow) | human | d5 | Id2, E7, myc, Nanog, Sox2, Ezh2 |
| lung epithelial cells | human | d1 | Id3, core, Lmo2, Ezh2 |
| lung epithelial cells | human | d2 | Id3, E7, E6, Yap1, Nanog |
| hepatocyte | murine | | c-myc, Klf4 |
| hepatocyte | murine | | Fos, E7, Klf4, Lmo2 |
| hepatocyte | murine | | TAg, Klf4 |
| hepatocyte | murine | | TAg, core, Klf4 |
| hepatocyte | murine | | Id3, Klf4, Id4 |
| hepatocyte | murine | | Fos, E7, Klf4 |
| hepatocyte | murine | | Fos, E7, Klf4, Id4 |
| hepatocyte | murine | | TAg, core |

It is evident from Table 5 that, as a generalised rule, the gene combinations suitable for cell immortalization each predominantly comprise a member of the Id gene family, a gene involved in maintaining pluripotency and a gene that facilitates the progression of the cell cycle. Therefore, it is envisaged that not certain individual genes are required for cell immortalisation, but genes from these categories. Accordingly, genes are substitutable with other genes of the same category. Suitable genes of the Id gene family are Id1, Id2, Id3, and Id4, suitable genes involved in maintaining pluripotency are Nanog, Sox1, Sox2, Sox3, Klf1, Klf2, Klf4, Klf5, Esrrb, Lin28, the miR290 cluster, Ecat1, Dppa5, ERas, Ecat8, Gdf3, Dppa4, Dppa2, Sall4, Oct3/4, Utf1, Tcl1, Dppa3, and suitable genes facilitating the progression of the cell cycle are E7, Fos, Jun, Myc, n-myc, h-ras, rat k-ras, RhoA, Rac1, Rac2, Rac3, Myb, beta-catenin, Core, Lmo2, E1a, E1b, E6, Sv40 large T antigen, Mdm2, Pim1, Pim2, Yap1, Gli1, Gli2, Gli3, E2F1, E2F2, E2F3, cyclin A, cyclin b, cyclin d, Suz12, Tbx2, Tbx3, Ezh2, Bmi1, Cbx7 and Rex.

Genes useful for immortalisation which do not fall into any of these categories are Bcl-2, Bcl-X1, HoxB4, Tlx1, vGPCR, HoxA9, Hoxb8, Stat3, ZFP217. These genes can be used to supplement the afore-mentioned combination of gene categories.

This feature of the technology can be used to establish designer cell lines. This is because every combination of immortalising genes confers slightly different properties to the respective cell line. This feature can be used to establish cell lines that are for example optimized for proliferation on a special surface coating or optimized for proliferation in a special cultivation media. For endothelial cells this feature of the described technology was used to identify gene combinations and thus establish cell lines that retain all functions and features of endothelial cells (see FIGS. 6, 7, 8 for the data). To identify the respective genes the technology was used to identify genes conferring immortalisation in the first round of infection. In the second round of infection these genes or subsets of genes were used for immortalisation. Importantly, the resulting cell lines were analysed with respect to their endothelial specific functions and features. From the most promising cell lines the combination of immortalisation genes were used in the third round of infection to immortalise HUVECs again (see FIG. 4 for an overview of the different combinations of immortalising genes). All combinations from this round of infection showed the desired properties for which examples are shown in the FIGS. 6, 7 and 8.

Example 5

Determining the Biological Relevance of the Established Cell Lines

The most important property of a cell line is its physiology which should as closely as possible resemble the physiology that the cell exhibits in vivo. Therefore the established cell lines were tested for their biological relevance. It is known that immortalisation often interferes with cellular signaling pathways.

As an example the interferon signaling was investigated. Type I interferons like the different Interferon α's or Interferon β are secreted proteins that are induced in response to pathogens like viruses, bacteria, or parasites. The type I interferons act either in an autocrine (on the secreting cell) or in a paracrine (on neighbouring cells) fashion. The interferons bind to the interferon receptor which induces downstream signalling by a trimeric complex composed of Stat1/Stat2 and IRF9. This complex translocates into the nucleus and binds to the promoters of the interferon inducible genes thereby activating their expression. Up to now approximately 2000 interferon inducible genes are identified. A well characterised interferon inducible gene is the MX2 gene. Therefore, the activation of interferon signalling can be indirectly measured by using a reporter system composed of the Mx2-promoter which drives the expression of the reporter gene luciferase.

Figure 5:
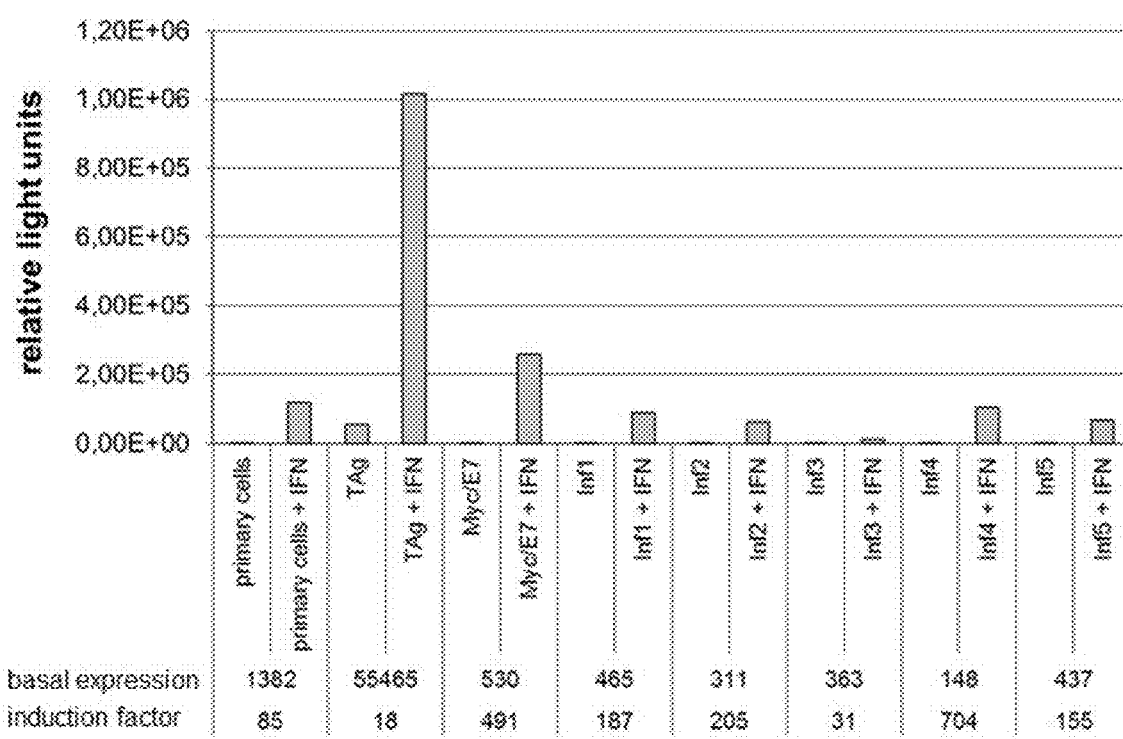
FIG. 5: Analysis of interferon signalling. Interferon signalling was monitored in murine ear fibroblasts which were isolated from transgenic MxLuc2 mice (Pulverer et al., J Virol. 2010 September; 84(17):8626-38.). Ear fibroblasts were isolated as described previously (May et al., J Biotechnol. 2005 Oct. 17; 120(1):99-110). Cell lines were established by conventional methods (with SV40 large T antigen—TAg) and by the technology described here. For this purpose the following immortalisation combinations were used (see examples for the composition of immortalising genes: 1-10=Inf1; 11-20=Inf2; 21-29=Inf3; MBG=Inf4; ALL=Inf5). The established cell lines and also the primary cells were cultivated with or without murine interferon (500 U/ml). After 24 h the cells were harvested and analysed for activity of luciferase to monitor the interferon signalling.

Such a genetic reporter construct was utilized to generate a reporter mouse. This mouse shows a strong induction of the luciferase reporter gene in response to interferon and also to different viruses. Importantly, the expression of the reporter protein in the absence of the inducers is hardly detectable (Pulverer et al., 2010, J Virol. 2010 September; 84(17):8626-38). The same induction profile is observed when primary cells are isolated from this mouse and treated with and without interferon. However, when a cell line from these primary cells is established by conventional methods like the immortalisation with the SV40 large T antigen, the expression characteristics are strongly influenced (FIG. 5).

The cell line immortalised with the SV40 large T antigen exhibits a higher basal expression of the reporter luciferase in the absence of the inducer interferon. Upon addition of interferon, the expression of luciferase is increased. However, the induction factor is much smaller compared to that of primary cells (FIG. 5). This proves that conventional immortalisation interferes strongly with interferon signalling.

Therefore, we applied the technology described here to establish novel cell lines which exhibit properties comparable to the in vivo situation. We tested the different cell lines that were generated for the expression of the reporter gene luciferase in the presence and absence of interferon. Several cell lines were established that showed induction characteristics of the interferon system that are similar to the in vivo situation which is characterized by a low luciferase expression without interferon that is strongly inducible upon interferon treatment (FIG. 5). The comparison of the induction factors of the different cell lines and the primary cells demonstrates that interferon signalling is altered in the cell line established by conventional immortalisation (with Sv40 large T antigen) whereas it is unaffected in primary cells as well as in the cell lines generated with the technology described here (FIG. 5).

Figure 6:
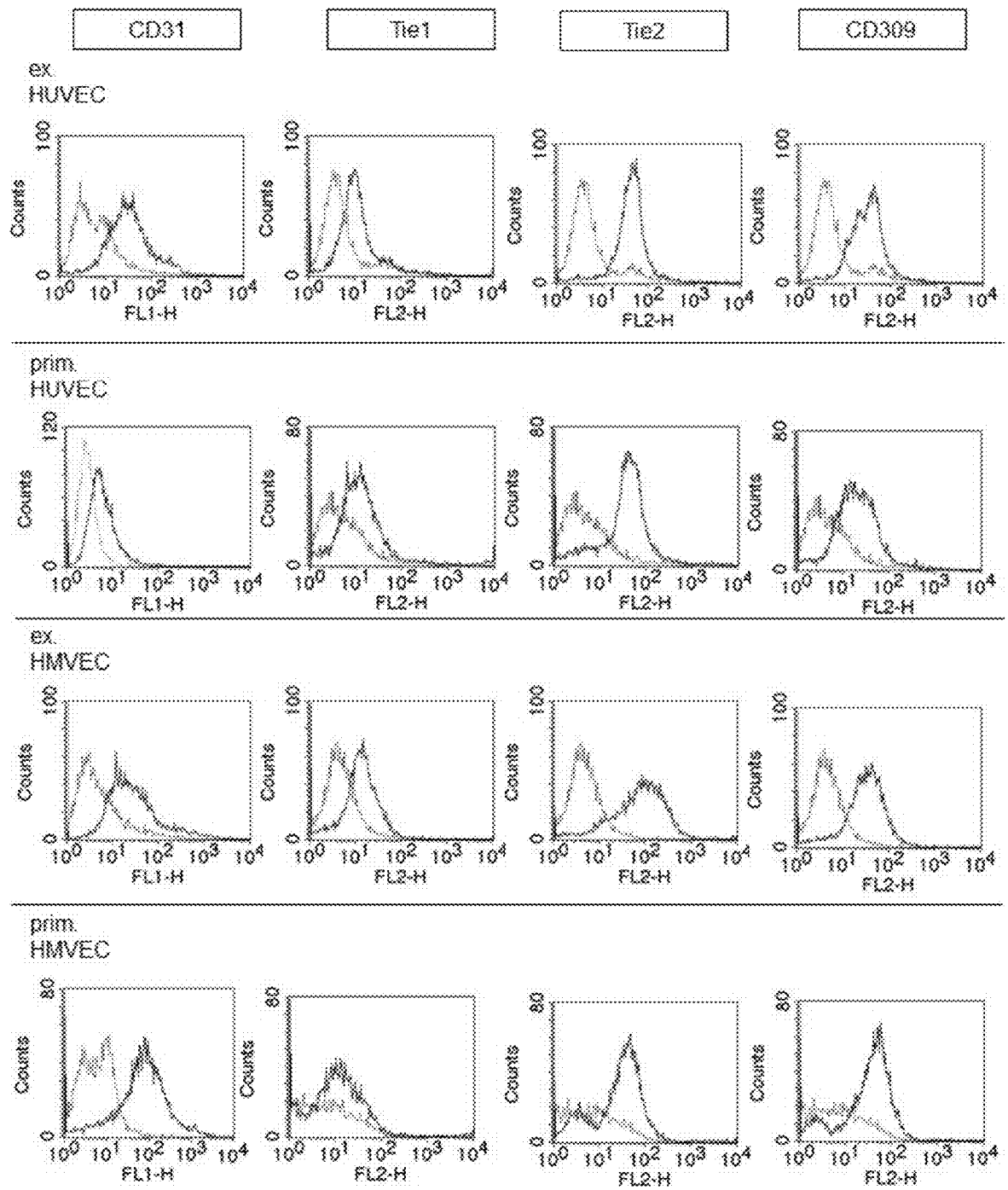
FIG. 6: Characterisation of the established endothelial cell lines. The established HUVEC and HMVEC cell lines were analysed for the expression of the endothelial specific surface markers (Pecam-1—CD31; Tie1; Tie2; VEGFR2—CD309). Shown are the data of a representative cell line. The HUVEC cell line (ex. HUVEC) was established through infection with fos, Id1 and Myc and analysed at a cumulative population doubling greater than 90. The HMVEC cell line (ex. HMVEC) was established through infection with Id1, Id2, Id3, Fos, TAg, E7, HoxA9, Myc, Nanog, Sox2, Ezh2, Gli1 and analysed at a cumulative population doubling greater than 40. As a comparison the same batch of primary HUVECs (prim. HUVEC) and primary HMVEC (prim. HMVEC) were included in this analysis. The expression of the respective marker proteins was determined by flow cytometry. The stained cells are shown in dark grey and the isotype control is shown in light grey.

Endothelial cells are specialised cells that line blood vessels. Endothelial cells can be comprehensively characterised with the help of marker proteins like the surface markers CD31, CD309, Tie1, or Tie2. The endothelial cell lines that were established with the technology described here were analysed for the expression of these markers. In this analysis, also primary cells were included to determine whether the established cell lines show a similar expression pattern of the respective markers (FIG. 6). The results demonstrate that the established endothelial cell lines are similar to the primary cells, i.e. the in vivo situation.

Figure 7:
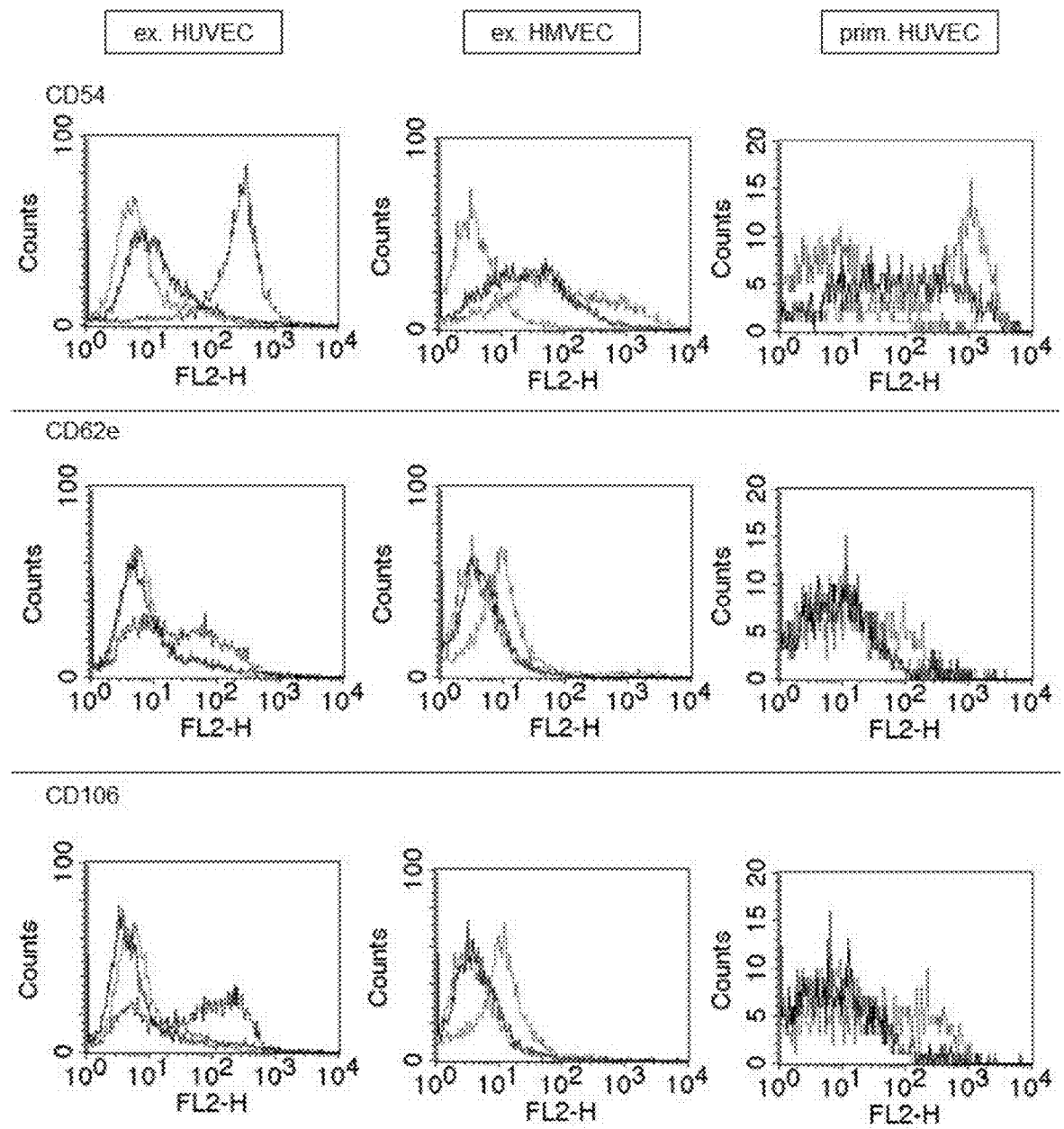
FIG. 7: Characterisation of the activated endothel. The established HUVEC and HMVEC cell lines were activated with or without TNFα (25 ng/ml) and analysed for markers of activated endothel. TNFα activates the endothel which can be measured by the upregulation of the surface markers CD54 (ICAM1), CD62E (E-Selectin), and CD106 (VCAM). Shown are the data of a representative cell line. The HUVEC cell line (ex. HUVEC) was established through infection with fos, Id1 and Myc and analysed at a cumulative population doubling greater than 40. The HMVEC cell line (ex. HMVEC) was established through infection with Id1, Id2, Id3, Fos, TAg, E7, HoxA9, Myc, Nanog, Sox2, Ezh2, Gli1 and analysed at a cumulative population doubling greater than 40. As a comparison, the same batch of primary HUVECs (prim. HUVEC) and primary HMVEC (prim. HMVEC) was included in this analysis. The expression of the respective marker proteins was determined by flow cytometry. Non-stimulated cells are shown in light grey, stimulated cells are shown in dark grey, the isotype control is represented by the dotted line.

Among the functions of the endothelial cells is the control of blood pressure, blood clotting and inflammatory processes. This is mainly mediated through their barrier function that restricts the transit of substances, small molecules, bacteria and also immune cells. From the site of an infection or an inflammation, proinflammatory cytokines like TNF-alpha are secreted, which activate the endothelium. This activation leads to an upregulation of certain surface molecules, which facilitate the binding and finally also the migration of immune cells through the endothelial cell layer. Surface molecules which are involved in this process are CD54 (ICAM1), CD62E (E-Selectin), and CD106 (VCAM). Therefore, the established endothelial cell lines were analysed for the expression of these surface molecules in the absence and presence of TNF-alpha. As a comparison, primary cells were included in this analysis. This analysis revealed that without the proinflammatory cytokine the surface molecules were hardly detectable and the stimulation with TNF-alpha led to an increase of the respective surface molecules (FIG. 7). The comparison of the results obtained from the primary cells with those obtained from the established cell lines reveals that both cell systems behave similarly as not the whole cell population responds uniformly to TNF-alpha but instead a subset of endothelial cells becomes activated (FIG. 7).

Figure 8:
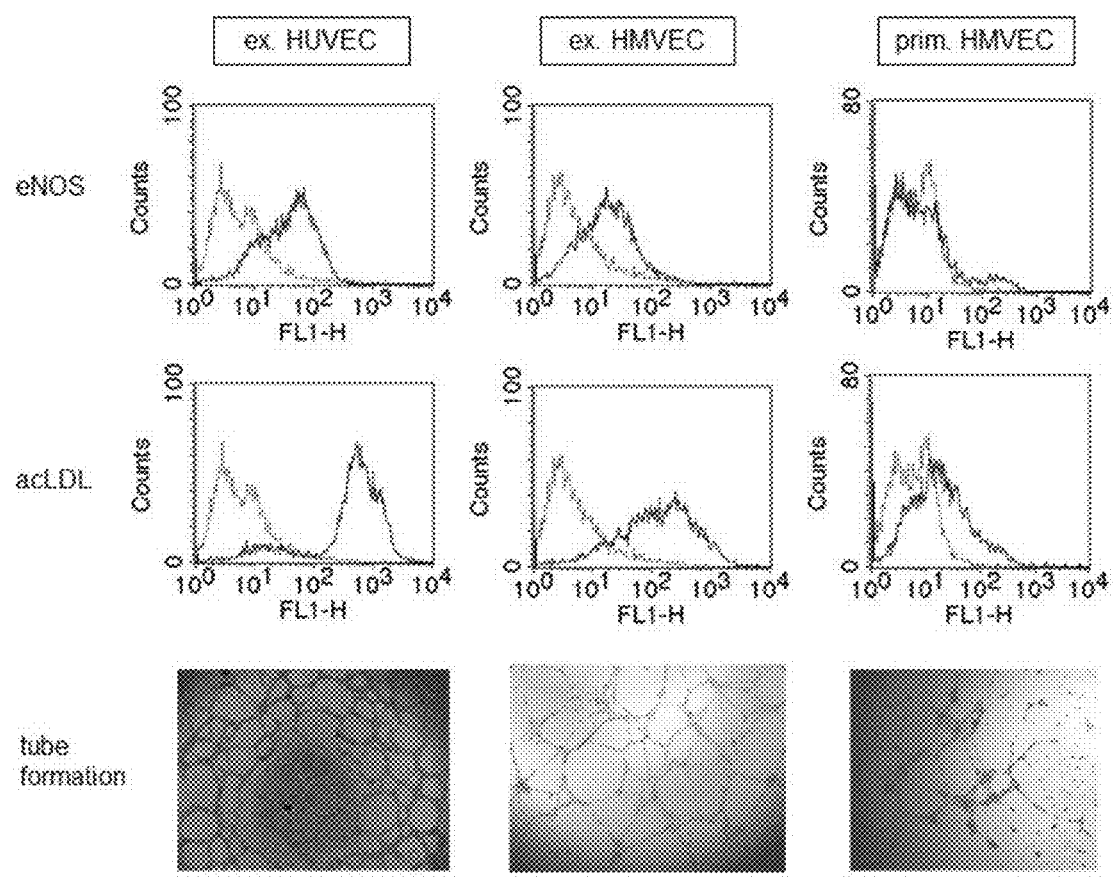
FIG. 8: Characterisation of endothel cell functions. The established HUVEC and HMVEC cell lines as well as primary HMVECs were analysed for endothelial specific functions. Part of the analysis was the determination of the activity of the eNos synthase, which produces the second messenger nitric oxide (eNOS), the uptake of acetylated low density lipoprotein (acLDL), and the determination of the angiogenic capacity, which is analysed by a matrigel assay (tube formation). Shown are the data of a representative cell line. The HUVEC (ex.HUVEC) cell line was established through infection with fos, Id1 and Myc and analysed at a cumulative population doubling greater than 40. The HMVEC cell line (ex.HMVEC) was established through infection with Id1, Id2, Id3, Fos, TAg, E7, HoxA9, Myc, Nanog, Sox2, Ezh2, Gli1 and analysed at a cumulative population doubling greater than 40. As a comparison, primary HMVEC (prim.HMVEC) were included in this analysis. The activity of the eNos synthase can be determined by flow cytometry with a eNos substrate (DAF-2 DA). This substrate is non-fluorescent and becomes fluorescent after conversion by the eNos synthase. Therefore, this conversion can be determined by flow cytometry (eNos row—light grey cells unstained; dark grey—cells incubated with DAF-2 DA). The uptake of acLDL can be determined by flow cytometry with a fluorescence labelled acLDL. Cells that take up acLDL become fluorescent as they accumulate acLDL (acLDL row—light grey cells unstained; dark grey—cells incubated with fluorescently labelled acLDL). The angiogenic capacity of cells can be measured by the formation of tubes on a matrigel coating. For this purpose, cell culture dishes were coated with matrigel. Upon this coating a single cell solution was added. The cells assembled into tube-like structures if they possessed angiogenic potenial (tube formation row).
Figure 9:
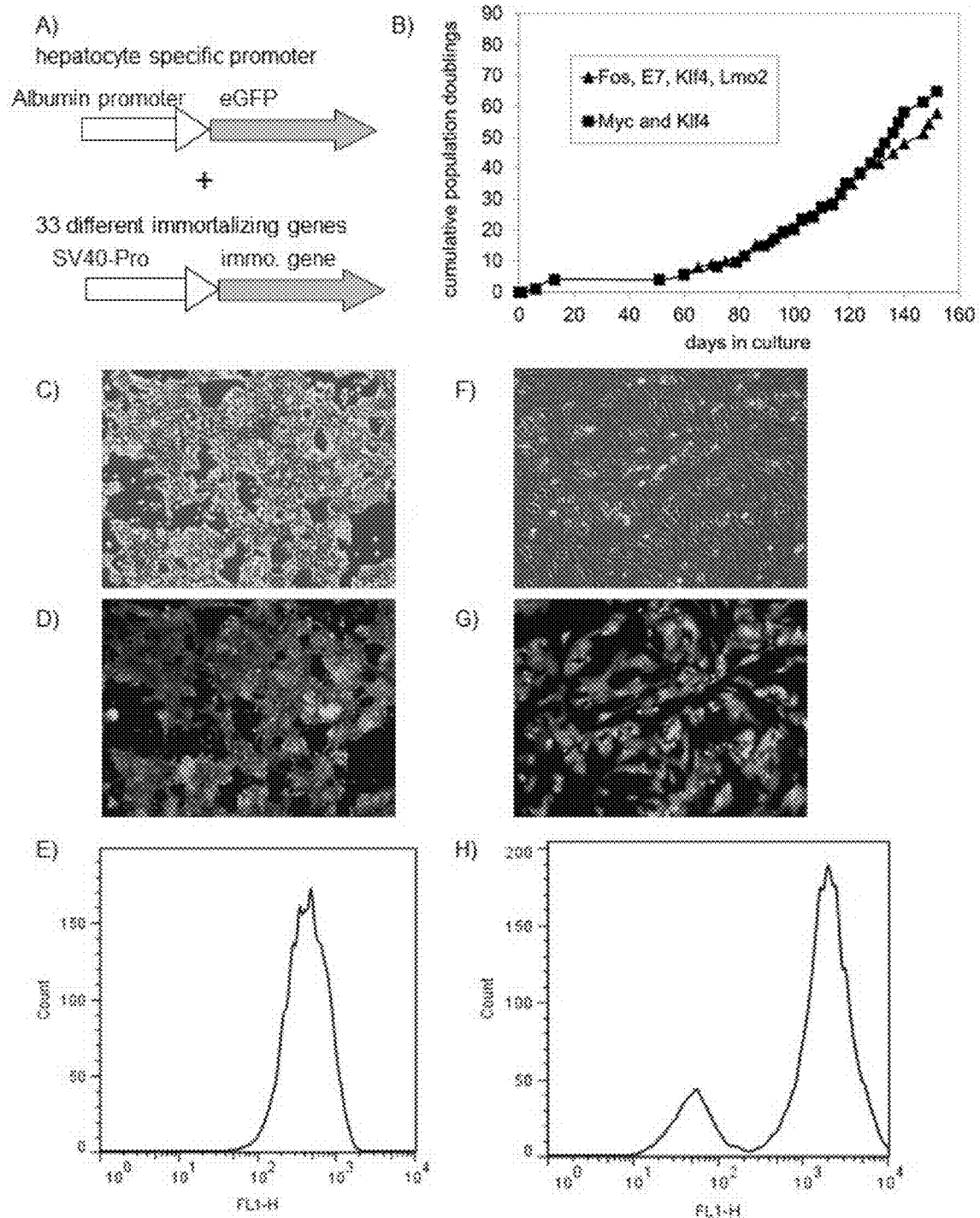
FIG. 9: Cell specific immortalization using a cell type specific promoter. Murine cells were isolated from the liver and infected with a mixture of lentiviruses. These self inactivating lentiviruses drive the expression of the 33 immortalizing genes from the constitutive but ubiquitous SV40 promoter. In contrast, the self inactivating lentivirus encoding the enhanced green fluorescent protein drives the expression of the transgene through the hepatocyte specific albumin promoter (A). Following the infection the primary cells were expanded and the cumulative population doublings were recorded demonstrating that the cell lines are immortalized. Shown are the cumulative population doublings for the cell lines established with c-myc and Klf4 (squares) and Fos, E7, Klf4, Lmo2 (triangles) (B). The established cell lines were further analyzed for eGFP expression to determine whether the established cell lines are of hepatocyte origin. For this purpose, bright field images (C; F) fluorescence images (D; G) and flow cytometry analysis (E; H) was performed. The cell line established by c-myc and Klf4 (C; D; E) showed a homogenous eGFP fluorescence signal. This proves that this cell line is derived of primary hepatocytes and shows hepatocyte function. The cell line established by Fos, E7, Klf4 and Lmo2 (F; G; H)

Also, other functions of endothelial cells like the development of new blood vessels, a process called angiogenesis, the production of the second messenger nitric oxide or the uptake of acetylated low density lipoprotein can be determined by in vitro assays. These assays were performed for the established endothelial cell lines as well as for primary cells. The different assays demonstrate that the established endothel cell lines retain all functions of normal endothel (FIG. 8).

For the analysis of surface markers, the endothelial cells were disaggregated with trypsin/EDTA and then incubated with monoclonal antibodies for specific endothelial cell markers: CD31; Tie1; Tie2; CD309; CD54; CD62e; CD106. The cells were incubated in 2% fetal calf serum in PBS for 30 minutes at room temperature with fluorescently labelled primary antibodies (CD31, CD309, CD54; CD62e, CD106). The concentrations of the antibodies were used according to the manufacturer's instructions. For unlabelled primary antibodies (Tie1, Tie2), the cells were washed with PBS after the first incubation (30 minutes at room temperature) followed by an incubation with a fluorescently labelled secondary antibody again for 30 minutes at room temperature. Afterwards, the cells were washed with 2% fetal calf serum in PBS, centrifuged and finally the cell pellet was resuspended in 2% fetal calf serum in PBS and analysed by flow cytometry.

For the uptake of acLDL, the cells were cultivated for 4 h at 37° C. with 4 µg/ml acLDL (labelled with Bodipy FITC, Molecular Probes). After the incubation, the cells were washed twice with PBS, disaggregated with trypsin/EDTA and centrifuged. The cell pellet was resuspended and analysed by flow cytometry. For the determination of the activity of the eNos synthase the cells were incubated for 30 minutes at room temperature with DAF-2 DA (1 µM). Afterwards the cells were washed twice with PBS, disaggregated with trypsin/EDTA and centrifuged. The cell pellet was resuspended and analysed by flow cytometry. For the analysis by flow cytometry a SSC/FSC dot blot was applied to exclude cell debris (FSC<200). The remaining gated cells were analysed for the respective fluorescence signals and plotted as histograms.

In vitro angiogenesis was monitored by a standard matrigel assay. Matrigel is a matrix rich product of Engelbert-Holm-Swarm tumor cells whose primary component is laminin. For the matrigel assay 96 wells were coated with Matrigel for 30 min at 37° C. $4*10^4$ cells were seeded per well and cultivated over night. Tube structure formation was evaluated by microscopic analysis.

Primary cells are isolated from tissue which is comprised of a different cell types. Thereby freshly isolated cultures of primary cells are very often heterogeneous concerning the cell types. If immortalization of a particular cell type is desired such cell type mixtures render the immortalization difficult. This stems from the fact that the different cell types possess different proliferation potential. In addition, the immortalization and transduction efficiencies differ tremendously between different cell types. An immortalization which is performed on primary cells directly isolated from tissue thereby preferentially establishes cell lines from the cell origin which is easy to transduce and shows the strongest proliferation. For most tissues this cell type is the fibroblast. To facilitate immortalization of a particular cell type from a mixture of cell types the technology described here can be combined with cell type specific promoters that drive the expression of a reporter gene.

For this purpose primary murine hepatocytes were isolated from liver tissue as detailed in Haridass et al. Am J Pathol. 2009 October; 175(4):1483-92. After isolation this cell type mixture was cultivated over night before the infection was performed. In addition to the lentiviral immortalization mix a lentivirus was included that drives the expression of the reporter gene eGFP from the albumin promoter which hepatocyte specific. The cell lines were established as described in example 3. Importantly, the albumin driven eGFP allowed throughout the experiments to distinguish between hepatic and non-hepatic cell lines. For this purpose the respective cell lines were either analyzed by fluorescence microscopy or by flow cytometry. For flow cytometric analysis the cells were washed with PBS, disaggregated with trypsin/EDTA, centrifuged and afterwards the cell pellet was resuspended. For the analysis by flow cytometry a SSC/FSC dot blot was applied to exclude cell debris (FSC<200). The remaining gated cells were analysed for the eGFP fluorescence signal and plotted as histograms. For fluorescence microscopy analysis the cells were plated on tissue culture plates and analyzed with a fluorescence microscope (Zeiss Axiovert 135TV) that was equipped with a filter set from OmegaOptical for eGFP visualization.

The invention claimed is:

1. A method for immortalizing cells with a finite life span, wherein the immortalized cells retain at least one differentiation-specific physiological property of the cells with a finite life span, comprising the following steps:
   (i) providing said cells with a finite life span,
   (ii) providing to said cells with a finite life span a combination of genes or gene products
   wherein said combination of genes or gene products and said cells with a finite life span are selected from the group consisting of
   (1) Id2, Fos, TAg, Id3, E7, Bcl2, Core, Id1, Myc, Lmo2, Yap1, Nanog, Sox2, Ezh2, Rex and human foreskin fibroblasts,
   (2) Id3, E7, Core, Id1, Myc, Lmo2, Yap1, Nanog, Ezh2, Rex and human foreskin fibroblasts,
   (3) core, Id1, Lmo2, Nanog and human foreskin fibroblasts,
   (4) RhoA, Ezh2 and human foreskin fibroblasts,
   (5) Id2, Fos, Id3, E7, core, Id1, Myc and human foreskin fibroblasts,
   (6) E7, Myc and human adult fibroblasts,
   (7) Myb, E7, HoxA9, Core, Myc and human adult fibroblasts,
   (8) Id2, Fos, βcat, TAg, Id3, E7, E6, HoxA9, Bmi1, core, K1f4, Id1, Myc, Lmo2, Nanog, Sox2, RhoA, Ezh2, Rex and murine adult ear fibroblasts,
   (9) Id2, Fos, Id3, core, K1f4, Id1, Nanog, Ezh2, Id4 and murine adult ear fibroblasts,
   (10) Id2, Fos, Id3 and murine adult ear fibroblasts,
   (11) K1f4, Id1, Lmo2, Yap1, Nanog and murine adult ear fibroblasts,
   (12) Sox2, Ezh2, Rex and murine adult ear fibroblasts,
   (13) Id2, Fos, Myb, Id3, E7, Id1, Myc, Nanog, Ezh2, Rex and human umbilical cord endothelial cells,
   (14) Fos, Id3, Bmi1, Yap1, Nanog and human umbilical cord endothelial cells,
   (15) Id2, Fos, Id3 and human umbilical cord endothelial cells,
   (16) Suz12, Id4, Rex and human umbilical cord endothelial cells,
   (17) Id2, Fos, βcat, TAg, E7, E6, Id1, Myc and human umbilical cord endothelial cells,
   (18) Id2, Fos, Id1, Myc and human umbilical cord endothelial cells,
   (19) Id2, Id1, Myc and human endothelial cells,
   (20) Id2, Fos, Id1 and human umbilical cord endothelial cells,
   (21) Fos, Id1, Myc, and human umbilical cord endothelial cells
   (22) Id2, Fos, Myc and human umbilical cord endothelial cells,
   (23) Id2, Fos, Myb, Id3, Bcl2 and human adult microvascular endothelial cells,
   (24) Id2, Fos, Id3, HoxA9, Id1, Nanog, Ezh2 and human adult microvascular endothelial cells,
   (25) Id1, Id3, Fos, Ezh2, Nanog and human adult microvascular endothelial cells,
   (26) E7, HoxA9, Sox2, Ezh2 and human adult microvascular endothelial cells,
   (27) Id1, Id3, Fos, TAg, E7, HoxA9, Nanog, Sox2, Ezh2 and human adult microvascular endothelial cells,
   (28) TAg, Id3, E7, E6, Lmo2, Nanog, Ezh2, ZFP217 and human cornea epithelial cells,
   (29) Id2, TAg, E7, Myc and human osteoblasts,
   (30) Fos, βcat, TAg, E7, Id1, Myc human osteoblasts,
   (31) Id2, Fos, TAg, E7, Myc and human osteoblasts,
   (32) Id2, Fos, Id3, E7, core, K1f4, Id1, Lmo2, Nanog, Sox2, Ezh2 and human chondrocytes,
   (33) Fos, Nanog, Ezh2 and human chondrocytes,
   (34) Id3, E7, Id1, Lmo2, Yap1, Nanog, Ezh2 and bovine macrophages,
   (35) Id2, Fos, Id1, Ezh2 and human adult keratinocytes,
   (36) Id2, Fos, E7, core, Lmo2, Nanog and human foreskin keratinocytes,
   (37) Id2, Fos, βcat, Id3, E7, Id1, Lmo2, Ezh2 and human foreskin keratinocytes,
   (38) Id2, E7, Nanog, Ezh2 and human foreskin keratinocytes,
   (39) Id2, Myb, Id3, E7, E6, Myc, Yap1, Nanog, Ezh2 and human bone marrow stroma cells,
   (40) Id2, Fos, Id3, E7, E6, core, Id1, Lmo2, Yap1, Nanog, Sox2, Ezh2 and human bone marrow stroma cells,

(41) Id2, Fos, E7, Id1, Lmo2, Yap1, Nanog, Sox2 and human bone marrow stroma cells,
(42) E7, E6, Bmi1, Id1, Myc, Lmo2, Yap1, Nanog, Sox2 and human bone marrow stroma cells,
(43) Id2, E7, myc, Nanog, Sox2, Ezh2 and human bone marrow stroma cells,
(44) Id3, core, Lmo2, Ezh2 and human lung epithelial cells,
(45) Id3, E7, E6, Yap1, Nanog and human lung epithelial cells,
(46) c-myc, K1f4 and murine hepatocytes,
(47) Fos, E7, K1f4, Lmo2 and murine hepatocytes,
(48) TAg, K1f4 and murine hepatocytes,
(49) TAg, core, K1f4 and murine hepatocytes,
(50) Id3, K1f4 and murine hepatocytes,
(51) Fos, E7, K1f4 and murine hepatocytes,
(52) Fos, E7, K1f4, Id4 and murine hepatocytes, or
(53) TAg, core and murine hepatocytes;
wherein cells of step (ii), which were provided with a combination of genes or gene products and as a result proliferate to an extent exceeding their natural proliferation capability in cell culture, are immortalized cells.

2. The method of claim 1, further comprising providing to said cells with a finite life span one or more gene products facilitating the selection of transduced cells.

* * * * *

SEQUENCE LISTING

```
<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: SV40 forward primer

<400> SEQUENCE: 1
ggaggcctag gcttttgcaa                                              20

<210> SEQ ID NO 2
<211> LENGTH: 20
<212> TYPE: DNA
<213> ORGANISM: Artificial Sequence
<220> FEATURE:
<223> OTHER INFORMATION: ID2 reverse primer

<400> SEQUENCE: 2
gcaggctgac aatagtggga                                              20

<210> SEQ ID NO 3
<211> LENGTH: 20
<212> TYPE: DNA
<213> ORGANISM: Artificial Sequence
<220> FEATURE:
<223> OTHER INFORMATION: Fos reverse primer

<400> SEQUENCE: 3
ggatgatgct gggaacagga                                              20

<210> SEQ ID NO 4
<211> LENGTH: 20
<212> TYPE: DNA
<213> ORGANISM: Artificial Sequence
<220> FEATURE:
<223> OTHER INFORMATION: NS1 reverse primer

<400> SEQUENCE: 4
atgtcctgga agagaaggca                                              20

<210> SEQ ID NO 5
<211> LENGTH: 20
<212> TYPE: DNA
<213> ORGANISM: Artificial Sequence
<220> FEATURE:
<223> OTHER INFORMATION: Jun reverse primer

<400> SEQUENCE: 5
ttcctcatgc gcttcctctc                                              20

<210> SEQ ID NO 6
<211> LENGTH: 20
<212> TYPE: DNA
<213> ORGANISM: Artificial Sequence
<220> FEATURE:
```

```
<223> OTHER INFORMATION: E2F1 reverse primer

<400> SEQUENCE: 6
cagggtctgc aatgctacga                                               20

<210> SEQ ID NO 7
<211> LENGTH: 20
<212> TYPE: DNA
<213> ORGANISM: Artificial Sequence
<220> FEATURE:
<223> OTHER INFORMATION: beta catenin reverse primer

<400> SEQUENCE: 7
ttatgcaagg tcccagcggt                                               20

<210> SEQ ID NO 8
<211> LENGTH: 20
<212> TYPE: DNA
<213> ORGANISM: Artificial Sequence
<220> FEATURE:
<223> OTHER INFORMATION: TAg reverse primer

<400> SEQUENCE: 8
cacctggcaa actttcctca                                               20

<210> SEQ ID NO 9
<211> LENGTH: 20
<212> TYPE: DNA
<213> ORGANISM: Artificial Sequence
<220> FEATURE:
<223> OTHER INFORMATION: Myb reverse primer

<400> SEQUENCE: 9
cttctggaag cttgtggcca                                               20

<210> SEQ ID NO 10
<211> LENGTH: 20
<212> TYPE: DNA
<213> ORGANISM: Artificial Sequence
<220> FEATURE:
<223> OTHER INFORMATION: Id3 reverse primer

<400> SEQUENCE: 10
atgacaagtt ccggagcgag                                               20

<210> SEQ ID NO 11
<211> LENGTH: 20
<212> TYPE: DNA
<213> ORGANISM: Artificial Sequence
<220> FEATURE:
<223> OTHER INFORMATION: E7 reverse primer

<400> SEQUENCE: 11
gcccattaac aggtcttcca                                               20

<210> SEQ ID NO 12
<211> LENGTH: 20
<212> TYPE: DNA
<213> ORGANISM: Artificial Sequence
<220> FEATURE:
<223> OTHER INFORMATION: E6 reverse primer

<400> SEQUENCE: 12
attcgccctt ttacagctgg                                               20
```

```
<210> SEQ ID NO 13
<211> LENGTH: 20
<212> TYPE: DNA
<213> ORGANISM: Artificial Sequence
<220> FEATURE:
<223> OTHER INFORMATION: Bcl2 reverse primer

<400> SEQUENCE: 13
tctgcgaagt cacgacggta                                                20

<210> SEQ ID NO 14
<211> LENGTH: 20
<212> TYPE: DNA
<213> ORGANISM: Artificial Sequence
<220> FEATURE:
<223> OTHER INFORMATION: HoxA9 reverse primer

<400> SEQUENCE: 14
gtttaatgcc ataaggccgg                                                20

<210> SEQ ID NO 15
<211> LENGTH: 20
<212> TYPE: DNA
<213> ORGANISM: Artificial Sequence
<220> FEATURE:
<223> OTHER INFORMATION: Bmi1 reverse primer

<400> SEQUENCE: 15
gggccatttc ttctccaggt                                                20

<210> SEQ ID NO 16
<211> LENGTH: 20
<212> TYPE: DNA
<213> ORGANISM: Artificial Sequence
<220> FEATURE:
<223> OTHER INFORMATION: PymT reverse primer

<400> SEQUENCE: 16
catctcgggt tggtgttcca                                                20

<210> SEQ ID NO 17
<211> LENGTH: 20
<212> TYPE: DNA
<213> ORGANISM: Artificial Sequence
<220> FEATURE:
<223> OTHER INFORMATION: core reverse primer

<400> SEQUENCE: 17
actttaccca cgttgcgcga                                                20

<210> SEQ ID NO 18
<211> LENGTH: 20
<212> TYPE: DNA
<213> ORGANISM: Artificial Sequence
<220> FEATURE:
<223> OTHER INFORMATION: Oct3 reverse prime

<400> SEQUENCE: 18
gcaaagcaga aaccctcgtg                                                20

<210> SEQ ID NO 19
<211> LENGTH: 20
<212> TYPE: DNA
<213> ORGANISM: Artificial Sequence
<220> FEATURE:
<223> OTHER INFORMATION: Klf4 reverse primer
```

<400> SEQUENCE: 19
aagatcaagc aggaggcggt                                          20

<210> SEQ ID NO 20
<211> LENGTH: 20
<212> TYPE: DNA
<213> ORGANISM: Artificial Sequence
<220> FEATURE:
<223> OTHER INFORMATION: Id1 reverse primer

<400> SEQUENCE: 20
agaagcacca aacgtgacca                                          20

<210> SEQ ID NO 21
<211> LENGTH: 20
<212> TYPE: DNA
<213> ORGANISM: Artificial Sequence
<220> FEATURE:
<223> OTHER INFORMATION: Myc reverse primer

<400> SEQUENCE: 21
agtgggctgt gaggaggttt                                          20

<210> SEQ ID NO 22
<211> LENGTH: 20
<212> TYPE: DNA
<213> ORGANISM: Artificial Sequence
<220> FEATURE:
<223> OTHER INFORMATION: Lmo2 reverse primer

<400> SEQUENCE: 22
tttccgtccc agcttgtagt                                          20

<210> SEQ ID NO 23
<211> LENGTH: 20
<212> TYPE: DNA
<213> ORGANISM: Artificial Sequence
<220> FEATURE:
<223> OTHER INFORMATION: Nfe2L2 reverse primer

<400> SEQUENCE: 23
gctgctgaag gaatcctcaa                                          20

<210> SEQ ID NO 24
<211> LENGTH: 20
<212> TYPE: DNA
<213> ORGANISM: Artificial Sequence
<220> FEATURE:
<223> OTHER INFORMATION: Yap1 reverse primer

<400> SEQUENCE: 24
gccaggatgt ggtcttgttc                                          20

<210> SEQ ID NO 25
<211> LENGTH: 20
<212> TYPE: DNA
<213> ORGANISM: Artificial Sequence
<220> FEATURE:
<223> OTHER INFORMATION: Nanog reverse primer

<400> SEQUENCE: 25
tatggagcgg agcagcattc                                          20

<210> SEQ ID NO 26
<211> LENGTH: 20

```
<212> TYPE: DNA
<213> ORGANISM: Artificial Sequence
<220> FEATURE:
<223> OTHER INFORMATION: Sox2 reverse primer

<400> SEQUENCE: 26
ctcgcagacc tacatgaacg                                              20

<210> SEQ ID NO 27
<211> LENGTH: 20
<212> TYPE: DNA
<213> ORGANISM: Artificial Sequence
<220> FEATURE:
<223> OTHER INFORMATION: RhoA reverse primer

<400> SEQUENCE: 27
aagcatttct gtcccaacgt                                              20

<210> SEQ ID NO 28
<211> LENGTH: 20
<212> TYPE: DNA
<213> ORGANISM: Artificial Sequence
<220> FEATURE:
<223> OTHER INFORMATION: Ezh2 reverse primer

<400> SEQUENCE: 28
acttcgagct cctctgaagc                                              20

<210> SEQ ID NO 29
<211> LENGTH: 20
<212> TYPE: DNA
<213> ORGANISM: Artificial Sequence
<220> FEATURE:
<223> OTHER INFORMATION: Gli1 reverse primer

<400> SEQUENCE: 29
caccacatca acagcgagca                                              20

<210> SEQ ID NO 30
<211> LENGTH: 20
<212> TYPE: DNA
<213> ORGANISM: Artificial Sequence
<220> FEATURE:
<223> OTHER INFORMATION: v-Myc reverse primer

<400> SEQUENCE: 30
gacaccctga gcgattcaga                                              20

<210> SEQ ID NO 31
<211> LENGTH: 20
<212> TYPE: DNA
<213> ORGANISM: Artificial Sequence
<220> FEATURE:
<223> OTHER INFORMATION: Suz12 reverse primer

<400> SEQUENCE: 31
taccctggaa gtcctgcttg                                              20

<210> SEQ ID NO 32
<211> LENGTH: 20
<212> TYPE: DNA
<213> ORGANISM: Artificial Sequence
<220> FEATURE:
<223> OTHER INFORMATION: ZFP217 reverse primer

<400> SEQUENCE: 32
```

-continued

```
caagaaggga gcaccgacaa                                              20

<210> SEQ ID NO 33
<211> LENGTH: 20
<212> TYPE: DNA
<213> ORGANISM: Artificial Sequence
<220> FEATURE:
<223> OTHER INFORMATION: Id4 reverse primer

<400> SEQUENCE: 33
cagcaaagtg gagatcctgc                                              20

<210> SEQ ID NO 34
<211> LENGTH: 20
<212> TYPE: DNA
<213> ORGANISM: Artificial Sequence
<220> FEATURE:
<223> OTHER INFORMATION: Rex reverse primer

<400> SEQUENCE: 34
gcgagctcat tacttgcagg                                              20
```